(12) United States Patent
Drapeau et al.

(10) Patent No.: US 9,289,375 B2
(45) Date of Patent: Mar. 22, 2016

(54) SKIN CARE COMPOSITIONS CONTAINING COMBINATIONS OF NATURAL INGREDIENTS

(75) Inventors: Christian Drapeau, San Clemente, CA (US); Shakahn Kukulcan, Auckland (NZ); Gitte S. Jensen, Port Dover (CA)

(73) Assignee: STEMTECH INTERNATIONAL INC., San Clemente, CA (US)

( * ) Notice: Subject to any disclaimer, the term of this patent is extended or adjusted under 35 U.S.C. 154(b) by 0 days.

(21) Appl. No.: 14/236,950

(22) PCT Filed: Aug. 3, 2012

(86) PCT No.: PCT/US2012/049619
§ 371 (c)(1),
(2), (4) Date: Feb. 4, 2014

(87) PCT Pub. No.: WO2013/022788
PCT Pub. Date: Feb. 14, 2013

(65) Prior Publication Data
US 2014/0227363 A1 Aug. 14, 2014

Related U.S. Application Data

(60) Provisional application No. 61/515,754, filed on Aug. 5, 2011.

(51) Int. Cl.
| | | |
|---|---|---|
| *A61K 36/00* | (2006.01) |
| *A61K 36/886* | (2006.01) |
| *A61K 36/82* | (2006.01) |
| *A61K 36/45* | (2006.01) |
| *A61K 36/752* | (2006.01) |
| *A61K 36/87* | (2006.01) |
| *A61K 35/74* | (2015.01) |
| *A61K 8/98* | (2006.01) |
| *A61K 8/60* | (2006.01) |
| *A61K 8/73* | (2006.01) |
| *A61Q 19/00* | (2006.01) |
| *A61Q 19/08* | (2006.01) |
| *A61K 8/896* | (2006.01) |
| *A61K 8/97* | (2006.01) |
| *A61K 8/99* | (2006.01) |
| *A61Q 19/02* | (2006.01) |

(52) U.S. Cl.
CPC . *A61K 8/986* (2013.01); *A61K 8/60* (2013.01); *A61K 8/73* (2013.01); *A61K 8/896* (2013.01); *A61K 8/97* (2013.01); *A61K 8/975* (2013.01); *A61K 8/99* (2013.01); *A61Q 19/00* (2013.01); *A61Q 19/007* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,419,962 B1 * | 7/2002 | Yokoyama et al. | 424/725 |
| 6,426,081 B1 | 7/2002 | Chong | |
| 2003/0039670 A1 | 2/2003 | Mizutani | |
| 2007/0003669 A1 * | 1/2007 | Kearl et al. | 426/72 |
| 2007/0122492 A1 | 5/2007 | Behr et al. | |
| 2007/0178061 A1 | 8/2007 | Venturi et al. | |
| 2008/0089941 A1 | 4/2008 | Mower | |
| 2009/0117061 A1 | 5/2009 | Gross | |
| 2009/0215720 A1 * | 8/2009 | Thibodeau et al. | 514/54 |
| 2009/0232892 A1 * | 9/2009 | Yamasaki et al. | 424/489 |
| 2010/0119463 A1 | 5/2010 | Jacobs | |
| 2010/0233128 A1 | 9/2010 | Panasenko | |
| 2012/0107252 A1 * | 5/2012 | Laza-Knoerr et al. | 424/59 |
| 2012/0195923 A1 * | 8/2012 | Turgeon et al. | 424/195.17 |
| 2012/0258059 A1 * | 10/2012 | Iwama et al. | 424/59 |
| 2013/0115195 A1 * | 5/2013 | Cappello | 424/93.4 |
| 2013/0190269 A1 * | 7/2013 | Thibodeau et al. | 514/54 |
| 2014/0005139 A1 * | 1/2014 | Yamasaki et al. | 514/53 |
| 2014/0113976 A1 * | 4/2014 | Matsumoto et al. | 514/773 |

FOREIGN PATENT DOCUMENTS

| | | |
|---|---|---|
| EP | 1306387 A1 | 5/2003 |
| WO | 20070084721 A2 | 7/2007 |
| WO | 20100048686 A1 | 5/2010 |
| WO | 2013022788 A1 | 2/2013 |

OTHER PUBLICATIONS

PCT/US2012/049619 International Search Report dated Sep. 28, 2012; 3 pages.
PCT/US2012/049619 Written Opinion dated Sep. 28, 2012; 4 pages.
PCT/US2012/049619 International Preliminary Report on Patentability dated Feb. 11, 2014; 5 pages.

* cited by examiner

*Primary Examiner* — Chris R Tate
(74) *Attorney, Agent, or Firm* — Stephen W. Chen; Nixon Peabody LLP

(57) ABSTRACT

Described herein are various natural ingredients for skin-related applications. Individual compounds provide beneficial effects for improved collagen production, fibroblast proliferation, antioxidant protection and free radical inhibition. Combinations of these individual compounds exhibit synergistic effects, leading to dramatic improvements in skin moisture levels, wrinkle reduction, and elasticity. Various examples of combined ingredients are provided, which can be applied in methods related to conditioning the skin, and in cosmetic formulations for improved aesthetic appearance.

15 Claims, 16 Drawing Sheets

Figure 7
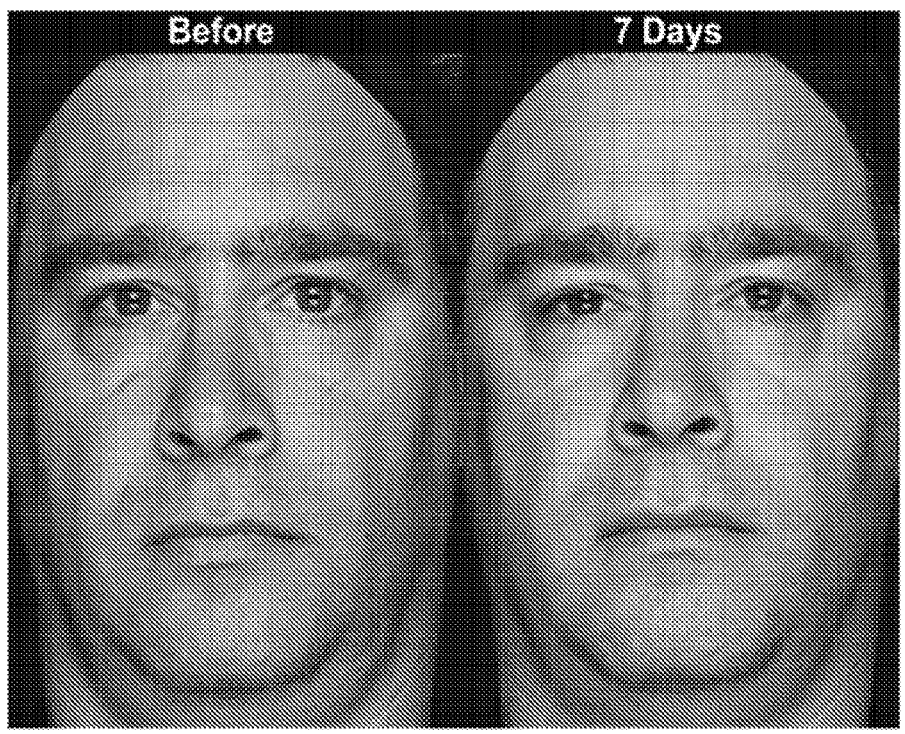

Figure 9   Before                    Day 28
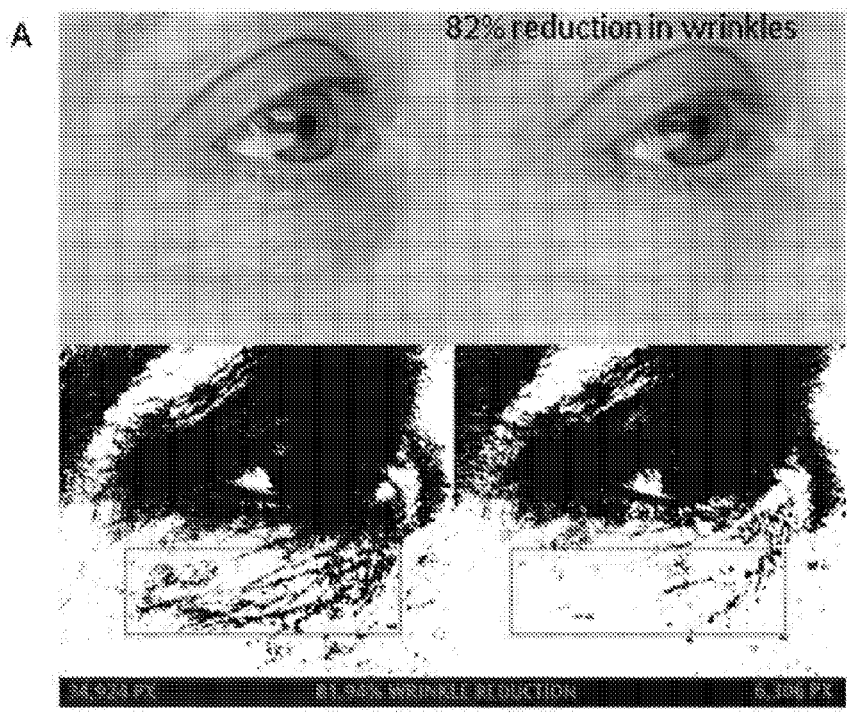
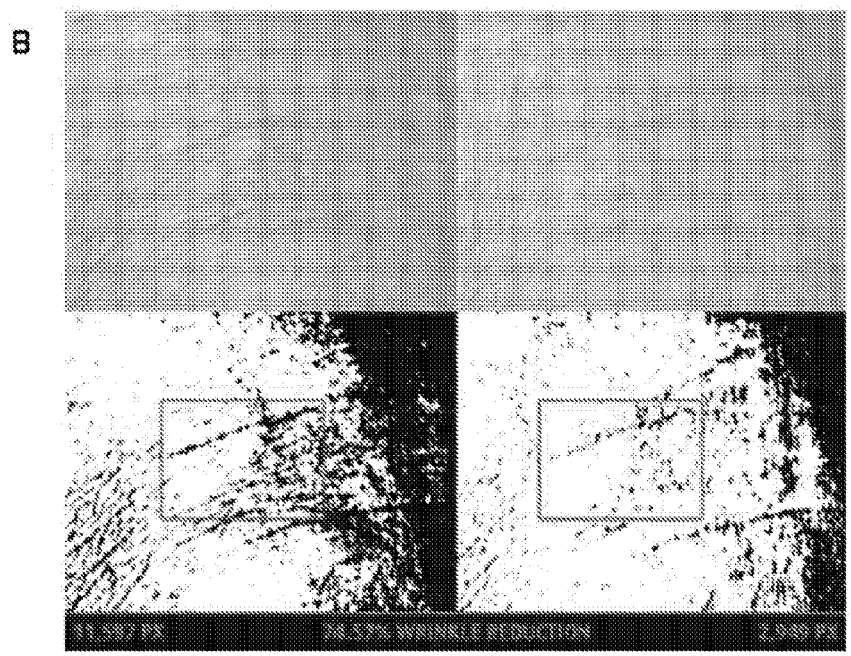

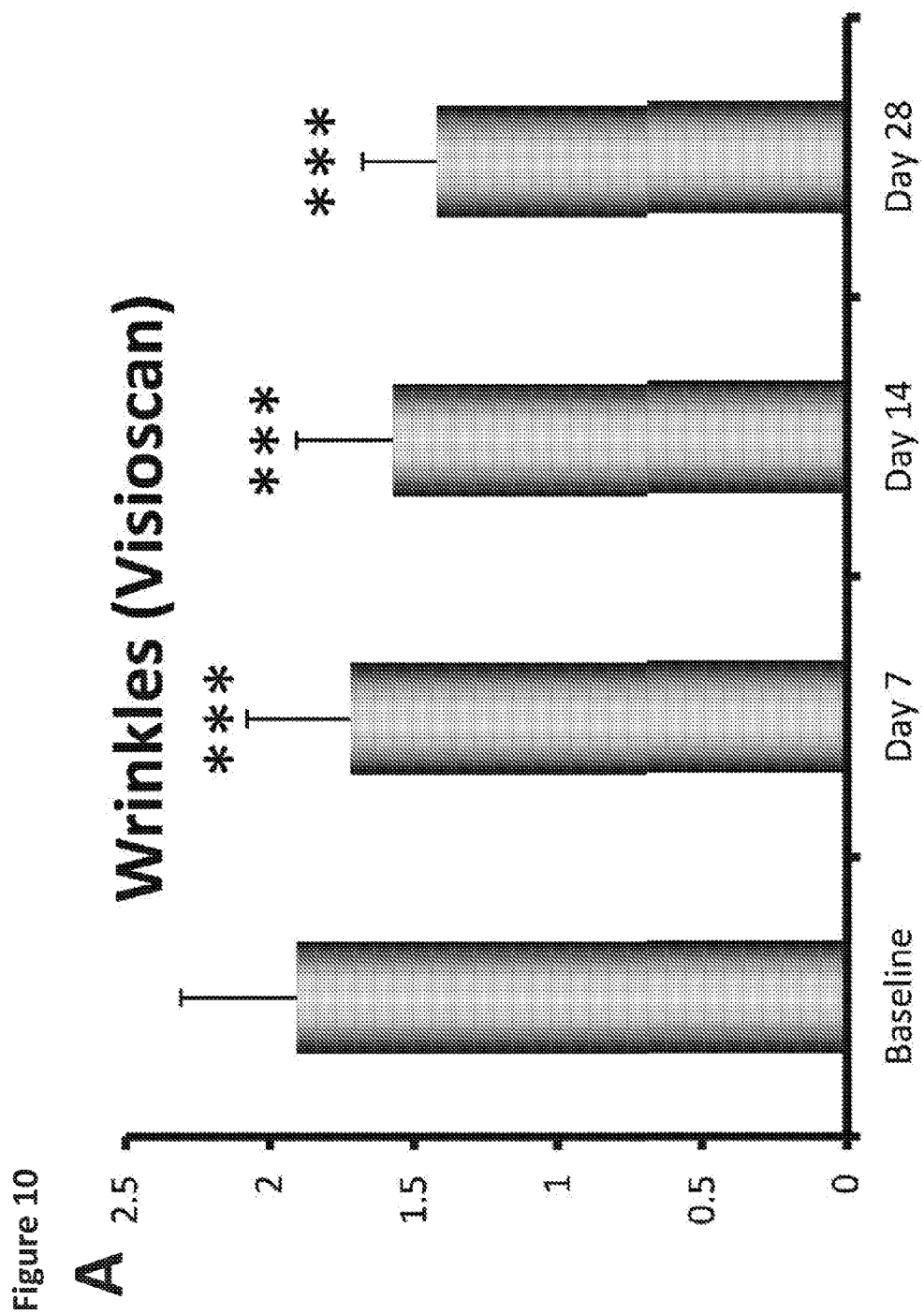

SKIN CARE COMPOSITIONS CONTAINING COMBINATIONS OF NATURAL INGREDIENTS

CROSS-REFERENCE TO RELATED APPLICATIONS

This application is a National Phase of International Application No. PCT/US2012/049619, filed Aug. 3, 2012, which designated the U.S. and that International Application was published under PCT Article 21(2) in English. This application also includes a claim or priority under 35 U.S.C. §119(c) to U.S. provisional patent application No. 61/515,754, filed Aug. 5, 2011.

FIELD OF THE INVENTION

This invention relates to the use of combinations of natural ingredients in skin-related applications.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Although compositions for skin care products operate through a variety of mechanisms, most provide only temporary moisture retention for improved hydration, transitory improvement in appearance and/or superficial relief of skin integrity.

Human skin is composed of three primary layers: the epidermis, dermis, and hypodermis. Each of these layers contains specific cell populations embedded within a complex physical and biochemical matrix, thereby providing the mechanical and functional organization necessary for the skin to maintain barrier function. It is well-known that the epidermis sloughs millions of cells every day, creating an enormous demand for replacement cells. Central to this process, which operates continuously throughout an organism's lifetime, are the various populations of progenitors and stem cells and the associated fibroblasts which provide biomechanical and trophic support. Progenitors and stem cells proliferate and differentiate as part of the natural repair and regeneration mechanism in the body, in order to meet this continual demand for new cells in the skin. Fibroblasts, which populate the dermis, provide vital trophic support, while producing important protein components of the skin.

There is a clear need in the art for compositions for skin care products, and methods of preparing skin care products, that have a proven capacity to directly act upon skin cells. This includes enhancement of proliferation and maintenance of skin cell populations for the purpose of promoting the skin repair and regenerative mechanisms in the body.

As described herein, the inventor has discovered new and useful compositions derived from natural ingredients in many of these plants act by supporting the proliferation, migration and differentiation of skin progenitor and stem cells and/or fibroblasts. These natural ingredients can be applied topically in a blended mixture (Coconut oil, Nilotica butter, *Rosa mosqueta*, Olivem 1000, Cocoa butter, Soy lecithin, Chilean Soapnut, NovHyal, Fucoidan Maritech, *Moringa, Aloe* vera, Genistein, Black mamaku, Cehami, Amla, AFA, Pomegranate, Sangre de drago, Guar, *Vanilla*, Colostrum, Cytokines, Maqui, Synergy berries, Green Tea Extract, *Vanilla* 20 fold extract, *Cacao*, Olive extract (Hydroxytyrolosol), Vitamin E (Sunflower), Samambaia, Bulgarian Rose, Jasmine, Sweet Orange, Ylang-ylang, Tangerine Essential Oil, Bitter Orange extract, and Honeysuckle), proved to have a significant effect on moisture retention in the skin, skin elasticity, as well as wrinkle reduction.

SUMMARY OF THE INVENTION

The present invention provides, in one embodiment, a purified skin care composition including one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, *Ceteryl olivate* or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof, and a cosmetically acceptable carrier. In another embodiment, the purified skin care composition is an emulsion substantially free of artificial ingredients.

Another aspect of the present invention provides, in one embodiment, a method of conditioning the skin of a subject including providing a quantity of a purified composition, wherein the composition including one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, *Ceteryl olivate* or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof, and administering a quantity of the purified composition to the subject in an amount sufficient to condition the skin of the subject. In another embodiment, conditioning the skin of the subject results in an increase in progenitor cell, stem cell, and/or dermal fibroblast proliferation. In another embodiment, conditioning the skin of the subject results in an increase in progenitor cell, stem cell, and/or dermal fibroblast mobilization. In another embodiment, conditioning the skin of the subject results in an increase in progenitor cell, stem cell, and/or dermal fibroblast migration. In another embodiment, conditioning the skin of the subject results in an increase in antioxidant protection. In another embodiment, conditioning the skin of the subject results in inhibition of free radical formation.

Another aspect of the present invention provides, in one embodiment, a method of improving skin appearance in a subject, including providing a quantity of a purified composition, wherein the composition includes one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, Ceteryl olivate or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof, and administering a quantity of the purified composition to the subject in an amount sufficient to improve skin appearance in a subject. In another embodiment, the improved skin appearance includes improved skin tone. In another embodiment, the improved skin appearance includes improved skin elasticity. In another embodiment, the improved skin appearance includes enhanced skin thickness. In another embodiment, the improved skin appearance includes improved skin hydration.

Another aspect of the present invention provides, in one embodiment, A method of reducing age-related features in the skin of a subject including providing a quantity of a purified composition, wherein the composition includes one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, Ceteryl olivate or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof, and administering a quantity of the purified composition to the subject in an amount sufficient to reducing age-related features in the skin of a subject. In another embodiment, age-related features include wrinkles. In another embodiment, the age-related features include fine lines. In another embodiment, the age-related features include dark patches of skin or age spots.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 7. depicts wrinkle reduction following short-term application. (A): Representative result of applying combination of natural ingredient over 7-day period. Measurements indicated a 74% reduction in wrinkles (B): Representative result of applying combination of natural ingredient over 7-day period. Measurements indicated a 81% reduction in wrinkles.

FIG. 9. depicts examples of wrinkle reduction following prolonged application. (A): Application of combination of ingredients over a 28 day period resulted in an 82% wrinkle reduction at the base of the eyelid. (B): Representative result of wrinkle reduction on the forehead as a result of topical application of the serum containing a combination of natural ingredients.

DETAILED DESCRIPTION

Figure 1:
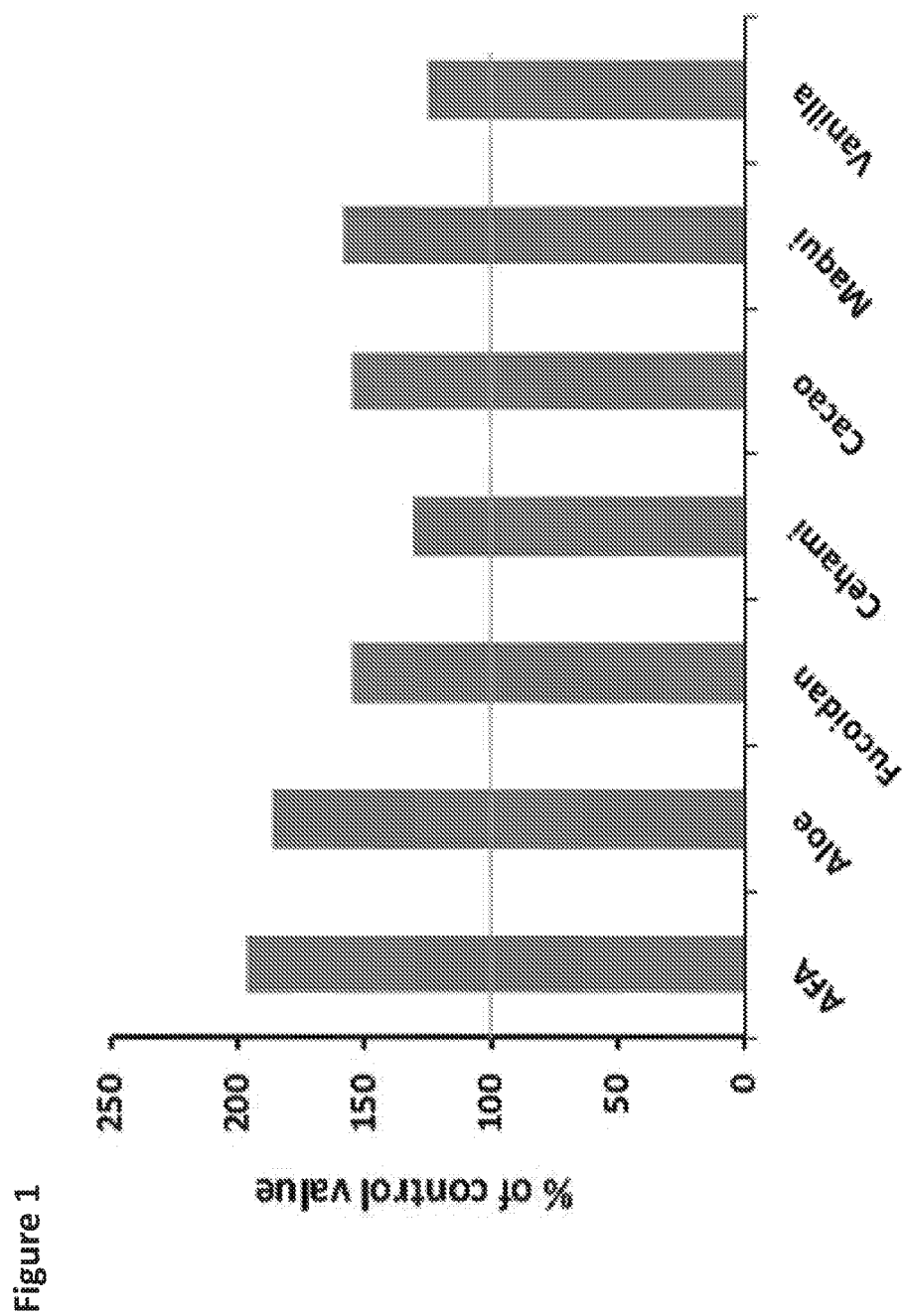
FIG. 1 depicts effects of individual compounds on cell proliferation. In neonatal dermal fibroblasts, a clear increase in proliferation of fibroblasts was observed for the following individual compound as described: *Aphanizomenon flos-aquae* (AFA) (96%), aloe (*Aloe Barbadensis*) (87%), fucoidan from *Undaria pinnatifida* (55%), cehami (*Centipeda cunninghamii*) (30%), cacao (*Theobroma cacao*) (54%), maqui berry (*Aristotelia chilensis*) (58%) and vanilla (*Vanilla planifolia*) (25%).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001); Dixon, *Plant Cell Culture: A Practical Approach*, Oxford University Press (U.S.A. 1994) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise.

Also, as used in the description herein, the meaning of "in" includes "in" and "on" unless the context clearly dictates otherwise.

"Artificial ingredients" as used herein refers to ingredients that are not found in nature and therefore must be synthetically produced as artificial ingredients. Examples includes additives commonly produced for the purpose of adding color, flavoring, taste, surfactants or emollients desired physical properties or preservatives for extended storage.

"Colostrum" as used herein refers to a fluid secreted by the mammary glands of female mammals during the first few days of lactation, containing various nutrients and protease inhibitors that keep it from being destroyed by the processes of digestion. Humans produce relatively small amounts of colostrum in the first two days after giving birth, but cows produce about nine gallons of colostrum.

"Cosmetically effective amount" as used herein is the quantity of a composition provided for administration and at a particular dosing regimen that is sufficient to achieve a desired appearance, feel, and/or protective effect. For example, an amount that results in the prevention of or a decrease in the appearance and/or symptoms associated with an undesirable condition, such as wrinkles, fine lines, skin thinness, loss of skin elasticity or suppleness, or other characteristics of skin associated with aging, UV, chemical exposure, adverse climate (e.g., temperature, humidity), dietary intake, biological agents, environmental oxidants, among others.

"Fucoidan" as used herein, describes sulfated fucans obtained from algae. Fucoidan has been obtained from a broad range Algae species as provided in the following non-exhaustive list: *Cladosiphon okamuranus, Chordaria flagelliformis, Ch. Gracilis, Saundersella simplex, Desmaestia intermedia, Dictyosiphon foeniculaceus, Dictyota dichotoma, Padina pavonica, Spatoglussum, schroederi, Adernocystis utricularis, Pylayella littoralis, Ascophyllum nodosum, Bifurcaria bifurcata, Fucus. Visculosus, F. spiralis, F. serratus, F. evaescens, Himanthalia lorea, Hizikia fusiforme, Pelvetia canaliculata, P. wrightii, Sargassum stenophyllum, S. honeri, S. Khellmanium, S. muticum, Alaria fistulosa, A. marginate, Arthrothammus bifidus, Chorda film, Ecklonia kurome, E. cava, Eisenia bicyclis, Laminaria angustata, L. brasiliensis, L. cloustoni, L. digitata, L. japonica, L. religiosia, L. saccharina, Macrocystis integrifolia, M pyrifera, Nereocystis luetkeana, Undaria pinnatifida, Petalonia fascia, Scytosiphon lomentaria*.

"Plant" and "plants" as used herein, include all species of the Kingdom Plantae, including plants under the Division Chlorophyta, Division Rhodophora, Division Paeophyta, Division Bryophyta and Division Tracheophyta; Subdivision Lycopsida, Subdivision Sphenopsida, Subdivision Pteropsida and Subdivision Spermopsida, Class Gymnospermae, Class Angiospermae, Subclass Dicotyledonidae and Subclass Monocotyledonidae. Plants include herbs, lower plants such as fungi and algae, and any organism colloquially known as a plant, fruit, or vegetable. Plants further include single cells, a plurality of cells, primary cell cultures, cell lines, cellular explants, individual organs, or any other cellular derivatives obtained from all species of Kingdom Plantae described herein. "Plant" and "plants" are used interchangeably herein with "botanical", wherein "botanical" includes all species of Kingdom Plantae described herein.

"Progenitor cell" as used herein refers to a cell that gives rise to progeny in a defined cell lineage.

"Subject" refers to a mammal, preferably a human, seeking to improve a condition, disorder or disease, including changes in aesthetic appearance, such as reduction/removal of undesirable aesthetic features (e.g., wrinkle reduction, improved hydration and elasticity of skin).

"Stem cell" as used herein refers to a cell that has the ability to divide (self replicate) for indefinite periods, often throughout the life of an organism, and which, under certain conditions or given particular signals, can differentiate to many different cell types that make up the organism. That is, stem cells have the potential to develop into mature cells that have characteristic shapes and specialized functions, such as keratinocytes, sebocytes, transit amplifying cells, or melanocytes. Stem cells may reside in the epithelial basal layer, interfollicular epidermis (IFE) niches, subaceous gland and hair follicle bulge.

Progenitor and Stem Cells in the Skin.

A classic example of the central role of progenitor and stem cells in skin repair and regeneration is that of keratinocyte stem cells (KSCs) maintaining epidermal barrier function (Mimeault and Batra, 2010). The epidermal barrier is characterized by a continual loss of terminally differentiated keratinocytes in the outermost epidermal layer, stratum corneum shed from the surface of the skin. KSCs that are located near the basement membrane of the innermost epithelial basal layer provide an essential role in replenishing of mature keratinocytes of epidermis, under both normal homeostatic conditions and in response to skin injury/wound healing. This is achieved by a characteristic asymmetric division of KSCs within the basal layer niche, resulting in both propagation of KSCs and more committed transit amplifying (TA)/intermediate cells. These TA cells then migrate outside the niche, giving rise to the terminally differentiated keratinocytes that constitute nearly 95% of cells found in various epidermal layers.

Although the skin contains wide potential for repair and regeneration, over an organism's lifetime, intrinsic and extrinsic factors combine to collectively alter the structural integrity and underlying repair and regenerative capacity of skin (Racila and Bickenbach, 2009). Aging of skin is characterized by loss of tone and elasticity, which may be coupled with increased epidermal dehydration, wrinkles, susceptibility to injury, and slow wound healing. A chief extrinsic factor causing accelerated skin-aging is UV exposure, wherein advanced exposure to UV light results in the cross-linking between skin proteins. Cross-linking of elastins and collagens, which are extracellular matrix ("ECM") proteins found in the skin, reduces reactivity with other skin matrix components, thereby reducing the optimal mechanical properties of skin. Simultaneously, more subtle molecular changes limit the self-renewal ability and regenerative capacity. For example, stem cells expressing melanoma chondroitin sulfate proteoglycan (MCSP) and $\beta 1$ integrins possess a high degree of self-renewal capacity, and expression of these markers is found to be drastically reduced in aging skin. In this regard, aging can be visualized as a multi-faceted process of change in both mechanical structure and a progressive reduction in underlying functional capacity.

Although keratinocytes are among the best known progenitor and stem cells supporting the populations of mature keratinocytes in the epidermis, a variety of other progenitor and stem cells are known to exist, performing specialized roles in the dynamic environment of skin maintenance, regeneration and repair. Importantly, many of these different types of progenitor and stem cell subpopulations are localized within very specific microenvironments located in the skin structure. For example, consider the different types of progenitor and stem cell subpopulations found within interfollicular epidermis (IFE) niches, subaceous gland and hair follicle bulge region niches. It appears that unipotent CK5/14 and BLIMP1 positive progenitor cells exist near the basement membrane surrounding the cutaneous sebaceous gland in the hair follicle. These cells have a primary role directed at regeneration of the subaceous gland, including terminal differentiation into sebocytes, which are responsible for sebum secretion. In contrast, the hair follicle bulge appears to contain multipotent epithelial stem cells (bESCs) that also give rise to mature keratinocytes, which in turn regenerate epidermal cells or repair epithelial tissue in response to injuries (Fuchs and Horsley, 2008). Further contrasting these two examples, the lower permanent portion of the bulge appears contain a population of melanocyte precursors, which play an important role in hair and skin pigmentation. In short, a complex interplay exists between the progenitor and stem cells found in these structures and their specific contribution to the maintenance of skin integrity and function.

Dermal Fibroblasts.

As the epidermis is avascular (i.e., not associated with or supplied by blood vessels), the primary means of supporting biological function is achieved through diffusion of nutrients by the underlying dermal layer. This layer is characterized by the presence of collagen and elastin fibers which provide mechanical structure of skin tissue, these ECM proteins themselves being produced by dermal fibroblasts. Reduced collagen production is characteristic of accelerated aging, in addition to post-translational modifications such as cross-linking caused by UV, as described above. While fibroblasts are the principal source of ECM in the skin, they are also a primary source of metalloproteinase proteins ("MMPs"), which are key molecules involved in degradation of ECM proteins. To the extent that MMP expression by fibroblasts is a normal process related to the natural turnover of ECM proteins in the skin, elevated MMP expression level by fibroblasts have been associated with accelerated aging. In turn, these higher levels of protein degrading enzymes lead to depletion and fragmentation of skin collagen, a reduction in collagen synthesis, depletion of growth factors and nutrients within reservoirs providing biotrophic support for skin cells, and diminished support from dermal fibroblasts and skin progenitor and stem cells within the basal lamina and epithelia. These observations affirm the view that aging is a combination of immediate, direct changes to the ECM protein structure and organization via elevated MMP activity, coupled with a gradual progressive decrease in regenerative capacity via diminished progenitor and stem cell activity. This progressive loss being the result of lowered mechanical and trophic support provided by fibroblasts establishing stem cell niche microenvironments.

Natural Ingredients.

A variety of anti-aging and skin care products exist on the market today. However, most of these compositions merely provide temporary improvement in skin hydration, tonicity and appearance, without tapping into the natural repair and regenerative mechanism in the body. Further, natural ingredients, when derived from animal and/or botanical sources, provides a renewable, non-toxic, and consistent source of materials from deriving skin care components.

A number of natural ingredients have been shown to have a beneficial effect on wound healing and the regeneration of the skin, though the mechanisms of action have often times remained unclear. For example, the capacity of genistein accelerate wound healing is only partially mediated via classical estrogen receptor-dependent signaling pathways, while the other mechanism of action remained unknown. *Phyllanthus emblica* was shown to accelerate wound healing, in part by supporting collagen formation and inhibiting matrix-metalloproteinase. A similar mechanism of action has been postulated for the beneficial effect of cacao on the skin. Support of immune functions was the hypothesis proposed for the mechanism of action underling the beneficial effect of *Undaria pinnatifida* on the healing of wounds associated with herpes. The benefits of green tea were shown to be partially mediated by polyphenols that would bring antioxidant protection and support the secretion of growth factors. The benefits of *Aloe barbadensis* were shown to be at least partially linked to the modulation of cytokines and growth factors in the skin. On the other hand, many others plants such as cehami (*Centipeda cunninghamii*), vanilla (*Vanilla planifolia*), *Aphanizomenon flos-aquae* (AFA), and black mamaku (*Cyathea medullaris*) have acquired a reputation for being beneficial to the skin without any valid scientific assessment.

As an expanded example demonstrates, fucoidan is a sulfated fucan with a demonstrated role in promoting regeneration and repair mechanism via promotion of blood stem cell activity. Further, it has been shown that fucoidan promotes collagen production in dermal fibroblasts, via elevated integrin. Given that shifting levels of collagen production are important steps in aging and wound healing, it is evident that natural ingredients such as fucoidan can serve as important components in compositions for enhancing skin care repair and regeneration by supporting the activity of progenitors and stem cells, as well as fibroblasts.

These many observations suggest that natural ingredients can serve as effective ingredients for reducing undesirable traits associated with aging and/or compounds for facilitating wound care in different skin care applications. However, the wide ranging types of important cellular actors and complexity of biochemical processes governing mechanisms of skin repair and regeneration, makes it less likely that a single natural ingredient can address the variety of factors causing progressive loss of desirable skin appearance, integrity and function. As such, without being bound by any theory, the inventor believes that combinations of natural ingredients provide important synergistic effects in supporting the many different processes involved in skin repair and regeneration. Whereas single ingredients may touch upon an important biochemical process leading to improved results, applying combination of more than one natural ingredient is more likely to provide synergistic effects to more rapidly and effectively engage with several different processes for improving skin repair and regeneration. A blended mixture (Coconut oil, Nilotica butter, *Rosa* mosqueta, Olivem 1000, Cocoa butter, Soy lecithin, Chilean Soapnut, NovHyal, Fucoidan Maritech, *Moringa, Aloe* vera, Genistein, Black mamaku, Cehami, Amla, AFA, Pomegranate, Sangre de drago, Guar, *Vanilla*, Colostrum, Cytokines, Maqui, Synergy berries, Green Tea Extract, *Vanilla* 20 fold extract, *Cacao*, Olive extract (Hydroxytyrolosol), Vitamin E (Sunflower), Samambaia, Bulgarian Rose, Jasmine, Sweet Orange, Ylang-ylang, Tangerine Essential Oil, Bitter Orange extract, and Honeysuckle), proved to have a significant effect on moisture retention in the skin, skin elasticity, as well as wrinkle reduction. This example demonstrates the effective results that may be achieved using a combination of natural ingredients.

Further, as an additional advantage, the various biochemical properties of natural ingredients allows their desirable features to be combined together at the exclusion of artificial ingredients. For example, pomengranate or extracts thereof can provide a desirable color and/or scent to a composition, without the use of a synthetic dye or flavoring. Likewise, *Croton lechleri* contains a natural elastic polymer component that can provide extensivility (i.e., spreadability), which could otherwise require the addition of a synthetic polymer. Similarly, *Aloe* extract, bitter orange extract from *Citrus*

*aurantium*, and honeysuckle extract from *Lonicera Japonica* all contain natural bacteriostatic properties, which reduces the need for synthetic preservatives or addition of a synthetic bacteriocide. Together, the different natural ingredients in a combined composition provide dual benefits: effective components for skin care conditioning, without the need for artificial ingredients for coloring, flavoring, taste, extended preservation, among other The present invention provides new compositions and methods for providing a wide range of cosmetic and/or therapeutic benefits for conditioning the skin by administering to a subject, compositions containing combinations of natural ingredients. In one embodiment, the topical skin care composition contains one or more of the following: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, *Ceteryl olivate* or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof and a cosmetically acceptable carrier. In another embodiment, the topical skin care composition is an emulsion substantially free of artificial ingredients.

In other embodiments, the composition includes one or more of the following natural ingredients in a specific amount (% w/w): Coconut oil purified from *Cocos nucifera* in an amount of about 0-10%, Nilotica butter purified from *Vitellaria nilotica* in an amount of about 0-3.6%, Rosa mosqueta purified from *Rosa rubiginosa* in an amount of about 0-3.6%, Olivem 1000 purified from *Ceteryl olivate* in an amount of about 0-6.0%, Cocoa butter purified from *Theobroma cacao* in an amount of about 0-3.6%, Soy lecithin purified from *Glycine Max* in an amount of about 0-1.6%, Chilean Soapnut purified from *Quillaja saponaria* in an amount of about 0-3.0%, NovHyal purified from NAG6P in an amount of about 0-4.0%, Fucoidan purified from *Laminaria japonica* in an amount of about 0-3.0%, Moringa purified from *Moringa oleifera* in an amount of about 0-3.0%, Aloe vera purified from *Aloe Barbadensis* in an amount of about 0-2.0%, Genistein purified from soy in an amount of about 0-1.33%, Black mamaku purified from *Cyathea medularis* in an amount of about 0-1.33%, Cehami purified from *Centipeda cunninghamii* in an amount of about 0-1.33%, Amla purified from *Phyllanthus emblica* in an amount of about 0-1.33%, AFA purified from *Aphanizomenon flos-aquae* in an amount of about 0-0.66%, Pomegranate purified from *Punica granatum* in an amount of about 0-0.66%, Sangre de drago purified from *Croton lechleri* in an amount of about 0-0.66%, Guar purified from *Cyamopsis tetragonolobus* in an amount of about 0-1.33%, Vanilla purified from *Vanilla planifolia* in an amount of about 0-1.33%, Colostrum purified from first milk in an amount of about 0-0.66%, Cytokines purified from *E. coli* in an amount of about 0-0.20%, Maqui purified from *Aristotelia chilensis* in an amount of about 0-0.50%, berries extract obtained from Wild Bilberry, Wild Ligonberry, Black Currant, Aronia, Pomegranate, Wild Blueberry, Concorde Grape, Sour Cherry, Wild Elderberry, Wild Cranberry, Red Raspberry, and/or Black Raspberry in an amount of about 0-0.50%, Green Tea Extract purified from *Camellia sinensis* in an amount of about 0-0.50%, Vanilla extract purified from *Vanilla planifolia* in an amount of about 0-0.44%, Cacao purified from *Theobroma cacao* in an amount of about 0-0.4%, Olive extract (Hydroxytyrolosol) purified from *Olea europaea* in an amount of about 0-2.0%, Vitamin E (Sunflower) purified from *Helianthus annuus* in an amount of about 0-1.6%, Samambaia purified from *Polypodium leucotomos* in an amount of about 0-1.0%, Bulgarian Rose purified from *Rosa damascena* in an amount of about 0-0.44%, Jasmine purified from *Jasminum grandiflorum* in an amount of about 0-0.48%, Sweet Orange purified from *Citrus sinensis* in an amount of about 0-0.80%, Ylang-ylang purified from *Cananga odorata* in an amount of about 0-0.24%, Tangerine Essential Oil purified from *Citrus reticulata* in an amount of about 0-0.020%, Bitter Orange extract purified from *Citrus aurantium* in an amount of about 0-2.5%, and/or Honeysuckle purified from *Lonicera japonica* in an amount of about 0-2.5% and combinations thereof. In different embodiments, the combinations of ingredient should constitute about 12-15% of the final composition volume.

The present invention further provides a method to condition the skin of a subject, including: providing a quantity of a composition, wherein the composition contains one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, *Ceteryl olivate* or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof and administering a quantity of the composition to the subject in an amount sufficient to condition the skin of the subject.

In another embodiment, conditioning the skin of the subject results in an increase in progenitor cell, stem cell and/or dermal fibroblast proliferation. In another embodiment, conditioning the skin of the subject results in an increase in progenitor cell, stem cell and/or dermal fibroblast mobilization. In another embodiment, conditioning the skin of the subject results in an increase in progenitor cell, stem cell and/or dermal fibroblast migration. In another embodiment, conditioning the skin of the subject results in protection from antioxidant damage. In another embodiment, conditioning the skin of the subject results in inhibition of free radical formation. In another embodiment, conditioning the skin of the subject results in enhanced collagen production. In another embodiment, conditioning the skin of the subject results in enhanced moisture retention, reduced appearance of fine lines, reduced appearance of wrinkles, reduced appearance of dark spots, age spots, improved complexion, improved skin tone, improved skin elasticity, enhanced healing of wounds, or enhanced skin thickness.

The present invention further provides a method of improving skin tone, improving skin elasticity, or enhanced skin thickness, including: providing a quantity of a composition, wherein the composition contains one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, *Ceteryl olivate* or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof; and administering a quantity of the composition to the subject in an amount sufficient to improve the skin tone, improve skin elasticity, or enhance thickness of the skin of the subject.

In another embodiment, improving skin tone, improving skin elasticity, or enhancing thickness of the skin of the subject results in an increase in progenitor cell, stem cell and/or dermal fibroblast proliferation. In another embodiment, improving skin tone, improving skin elasticity, or enhancing thickness of the skin of the subject is characterized by an increase in progenitor cell, stem cell and/or dermal fibroblast mobilization. In another embodiment, improving skin tone, improving skin elasticity, or enhancing thickness of the skin of the subject is characterized by an increase in progenitor cell, stem cell and/or dermal fibroblast migration. In another embodiment, improving skin tone, improving skin elasticity, or enhancing thickness of the skin of the subject is characterized by protection from antioxidant damage. In another embodiment, improving skin tone, improving skin elasticity, or enhancing thickness of the skin of the subject is characterized by inhibition of free radical formation. In another embodiment, improving skin tone, improving skin elasticity, or enhancing thickness of the skin of the subject is characterized by enhanced collagen production. In another embodiment, improving skin tone, improving skin elasticity, or enhancing thickness is characterized by enhanced moisture retention.

The present invention further provides a method of reducing the appearance of fine lines or reducing the appearance of wrinkles, including: providing a quantity of a composition, wherein the composition contains one or more of the following components selected from the group including: fucoidan or extracts thereof, *Moringa oleifera* or extracts thereof, *Aloe* or extracts thereof, soy or extracts thereof, *Cyathea medularis* or extracts thereof, *Centipeda cunninghamii* or extracts thereof, *Phyllanthus emblica* or extracts thereof, *Aphanizomenon flos-aquae* or extracts thereof, *Punica granatum* or extracts thereof, *Croton lechleri* or extracts thereof, colostrum or extracts thereof, *Citrus aurantium* or extracts thereof, *Lonicera japonica* or extracts thereof, *Olea europaea* or extracts thereof, *Polypodium leucotomos* or extracts thereof, *Camellia sinensis* or extracts thereof, *Aristotelia chilensis* or extracts thereof, berries or extracts thereof, *Theobroma cacao* or extracts thereof, *Cocos nucifera* or extracts thereof, *Vitellaria nilotica* or extracts thereof, *Rosa rubiginosa* or extracts thereof, *Ceteryl olivate* or extracts thereof, *Theobroma cacao* or extracts thereof, *Glycine max* or extracts thereof, *Citrus sinensis* or extracts thereof, *Quillaja saponaria* or extracts thereof, *Helianthus annuus* or extracts thereof, NAG6P, *E. coli* or extracts thereof, *Rosa damascena* or extracts thereof, *Jasminum grandiflorum* or extracts thereof, *Cananga odorata* or extracts thereof, *Citrus reticulata* or extracts thereof, and/or *Vanilla* or extracts thereof; and administering a quantity of the composition to the subject in an amount sufficient to reduce the appearance of fine lines or reduce the appearance of wrinkles in the skin of the subject.

In another embodiment, reducing the appearance of fine lines or reducing the appearance of wrinkles in the skin of the subject results in an increase in progenitor cell, stem cell and/or dermal fibroblast proliferation. In another embodiment, reducing the appearance of fine lines or reducing the appearance of wrinkles in the skin of the subject is characterized by an increase in progenitor cell, stem cell and/or dermal fibroblast mobilization. In another embodiment, reducing the appearance of fine lines or reducing the appearance of wrinkles in skin of the subject is characterized by an increase in progenitor cell, stem cell and/or dermal fibroblast migration. In another embodiment, reducing the appearance of fine lines or reducing the appearance of wrinkles in the skin of the subject is characterized by protection from antioxidant damage. In another embodiment, reducing the appearance of fine lines or reducing the appearance of wrinkles in the skin of the subject is characterized by inhibition of free radical formation. In another embodiment, reducing the appearance of fine lines or reducing the appearance of wrinkles in the skin of the subject is characterized by enhanced collagen production. In another embodiment, reducing the appearance of fine lines or reducing the appearance of wrinkles is characterized by enhanced moisture retention. In another embodiment, frequency and depth of wrinkles can be measured using Visioscan imaging. In another embodiment, skin elasticity can be measured using a cutometer. In another embodiment, skin hydration can be measured using a dermal phase meter.

In various embodiments, the composition is formulated for topical application to the skin, such as the skin surrounding or including the eyes, mouth, nose, forehead, ears, neck, hands, feet, hair, and/or overall body. For example, the topical skin care composition may be in the form of a solution, serum, cream, lotion, body milk, emulsion, balm, gel, soap, conditioner, powder and the like. Alternatively, the topical skin care composition may be in the form of a shampoo, conditioner, serum, or toner. In other embodiments, the composition is formulated for topical application to hair or scalp.

In other embodiments, the composition is provided as an active ingredient in a composition formulated for topical application to the skin. In other embodiments, the composition is provided as an active ingredient in a composition formulated for topical application to hair or scalp. In other embodiments, the composition is provided as an active ingredient in a composition formulated for use in wound healing. In other embodiments, the composition is provided as an active ingredient in a composition formulated for cosmetic use. In other embodiments, the composition is provided as an active ingredient in a composition formulated for use as a conditioning product for a subject seeking to improve their appearance. Various skin-related conditions include appearance of aging, wrinkles, fine lines, thinness, diminished elasticity or suppleness, dry skin, undesirable appearance of pores, pronounced appearance of stretch marks and scars, undesirable color tone and hue, dermatitis, eczema, sunburn, inflammation, pruritic lesions, inflammatory and non-inflammatory lesions of the skin of a subject. Other conditions related to hair include baldness (i.e., alopecia), reduced shaft volume, structural deformations (e.g., split ends), low elasticity, brittleness, dullness, dryness, slow growth, among others.

EXAMPLES

Example 1

Sources of Natural Ingredients

Natural ingredients may be purified or isolated from a variety of plant and animal sources. For example, black mamaku, is an extract prepared from a black tree fern (*Cyathea medullaris*) endemic to New Zealand. Cehami, is an indigenous herb (*Centipeda Cunninghamii*) found in Australia. Pomegranate is a fruit-bearing tree (*Punica granatum*) from Central Asia. *Croton lechleri*, also known as Sangre de Grado (Dragon's blood), is a plant native to South America, whose latex is used by native peoples for wound healing. Cacao (*Theobroma cacao*) is the fruit-bearing tree whose seeds are used to make cocoa powder and chocolate. Maqui (*Aristotelia chilensis*) is a tree which produces berries and is found in Argentinian rainforest. Green tea (*Camellia sinensis*) has long been cultivated in Asia as a source of ingredients that provide various health benefits. Vanilla is obtained from orchids of the genus *Vanilla*, a native plant from Mexico. Fucoidan describes sulfated fucans obtained from algae, such as *Undaria pinnatifida*. *Aphanizomenon flos-aquae* (AFA) is a blue-green algae known to contain a variety of antioxidants and other biologically active compounds. Aloe may be obtained from species of the genus *Aloe*, a leafy plant originating from Africa, examples of *Aloe* species include *Aloe barbadensis* and *A. Africana*. Mushroom polysaccharides are glucans found mainly in various species of mushrooms such as *Cordyceps sinesis, Hercicium erinaceous*, and *Ganoderma lucidum*. Colostrum is a fluid secreted by the mammary glands of female mammals during the first few days of lactation, a primary source being bovine animals. The specific structures or forms from which natural ingredients are derived from these species are obtained (e.g., leaf, bean, fruit, bark, etc.) are described in Tables 2 and 3.

Example 2

Natural Ingredients Isolated from Plants Increase Fibroblast Proliferation

Figure 2:
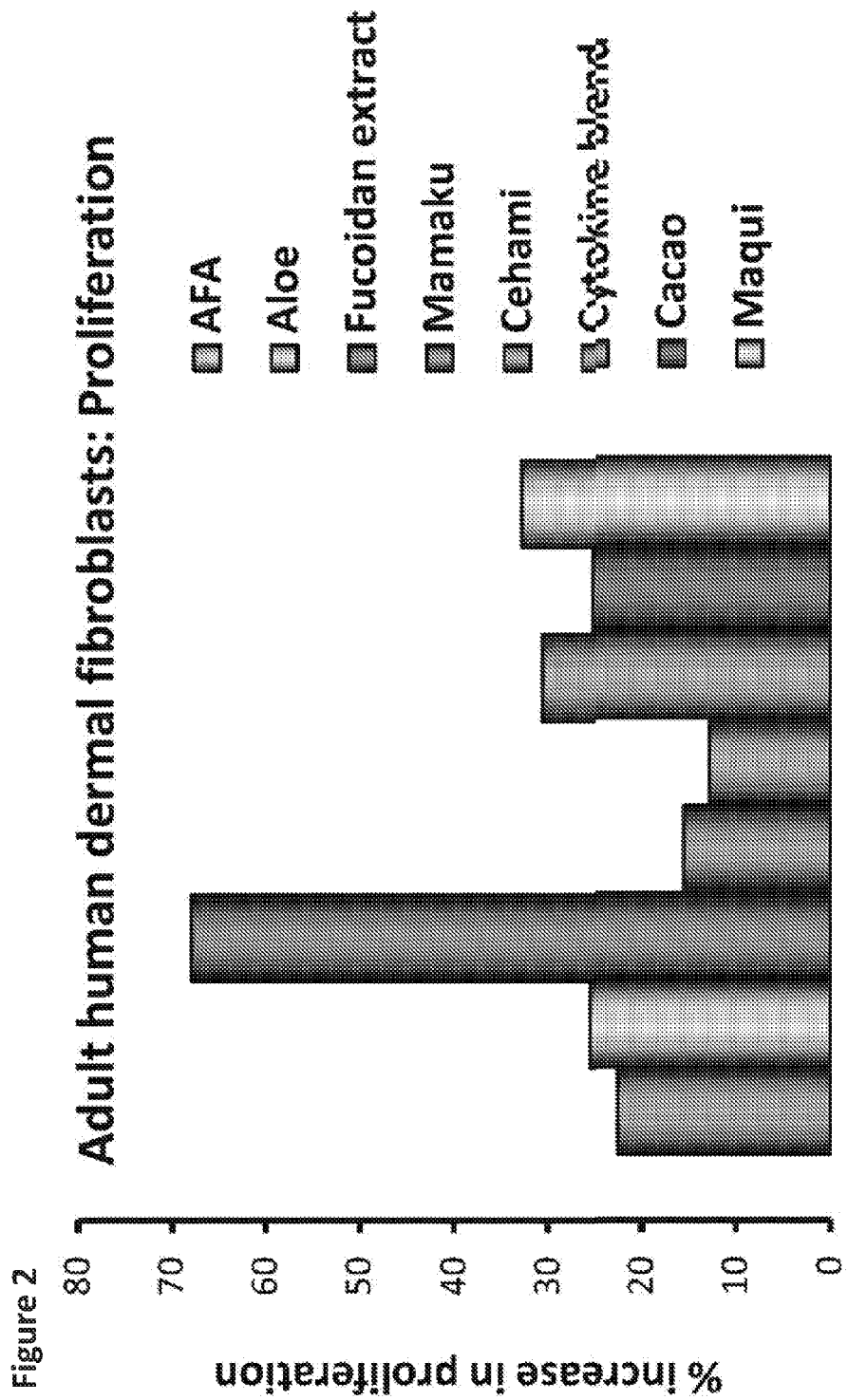
FIG. 2 depicts effects of individual compounds on cell proliferation. In adult human dermal fibroblasts, *Aphanizomenon flos-aquae* (AFA), aloe (*Aloe Barbadensis*), fucoidan from *Undaria pinnatifida*, black mamaku (*Cyathea medullaris*), cehami (*Centipeda cunninghamii*), cytokine blend, cacao (*Theobroma cacao*), and maqui berry (*Aristotelia chilensis*) significantly increase dermal fibroblast proliferation, ranging from an increase of over 10% up to nearly 70% across various compounds. Vanilla (*Vanilla planifolia*) and colostrum did not significantly increase adult dermal fibroblast proliferation on their own but synergistically potentiated the effect of AFA. A blend of cytokines, including epidermal growth factor, fibroblast growth factors, keratinocytes growth factor, hepatocyte growth factors, and stem cell factor, led to substantial increase in dermal fibroblast proliferation above baseline.

As shown in FIG. 1, the following plants increased the proliferation of neonatal dermal fibroblasts: AFA (96%), aloe (87%), fucoidan from *Undaria pinnatifida* (55%), cehami (30%), cacao (54%), maqui (58%) and vanilla (25%). As shown in FIG. 2, these results were extendible into adult fibroblasts cultured in vitro. Individual compounds enhanced cell proliferation ranging from an increase of over 10% up to nearly 70% across various compounds when compared to untreated controls, thereby demonstrating a substantial increase in dermal fibroblast proliferation above baseline.

Example 3

Synergetic Effects Achieved Using Combinations of Natural Ingredients

Figure 3:
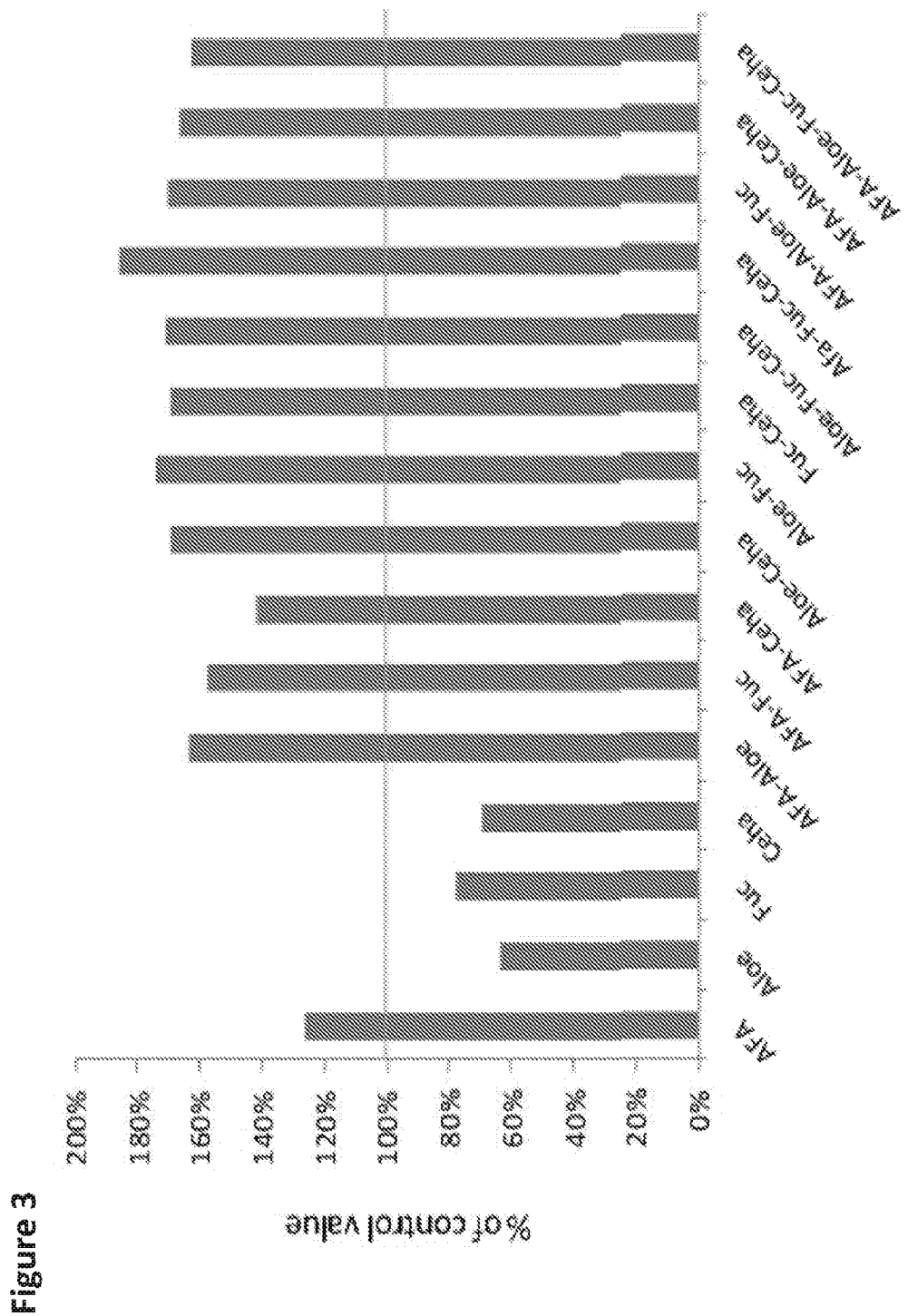
FIG. 3 depicts the effect of combinations of compounds. In adult dermal fibroblasts, individual compounds clearly demonstrated synergistic effects when blended together in enhancing the proliferation. AFA enhanced the proliferation of adult dermal fibroblasts by 26%. However, aloe (*Aloe Barbadensis*), fucoidan from *Undaria pinnatifida* and cehami (*Centipeda cunninghamii*) individually reduced proliferation by 37%, 22% and 30%, respectively. When combined, blends of these various ingredients enhanced proliferation by 42% to 86%. Most significant effects were observed for blends of AFA, fucoidan and cehami (86%), aloe and fucoidan (74%), aloe, fucoidan, and cehami (71%), fucoidan and cehami (70%), AFA, aloe and fucoidan (70%), and a blend of all four ingredients (63%). Blending of AFA with cacao (*Theobroma cacao*) and vanilla (*Vanilla planifolia*) also created a synergy that increased the proliferation adult dermal fibroblasts by 30% and 15%.
Figure 4:
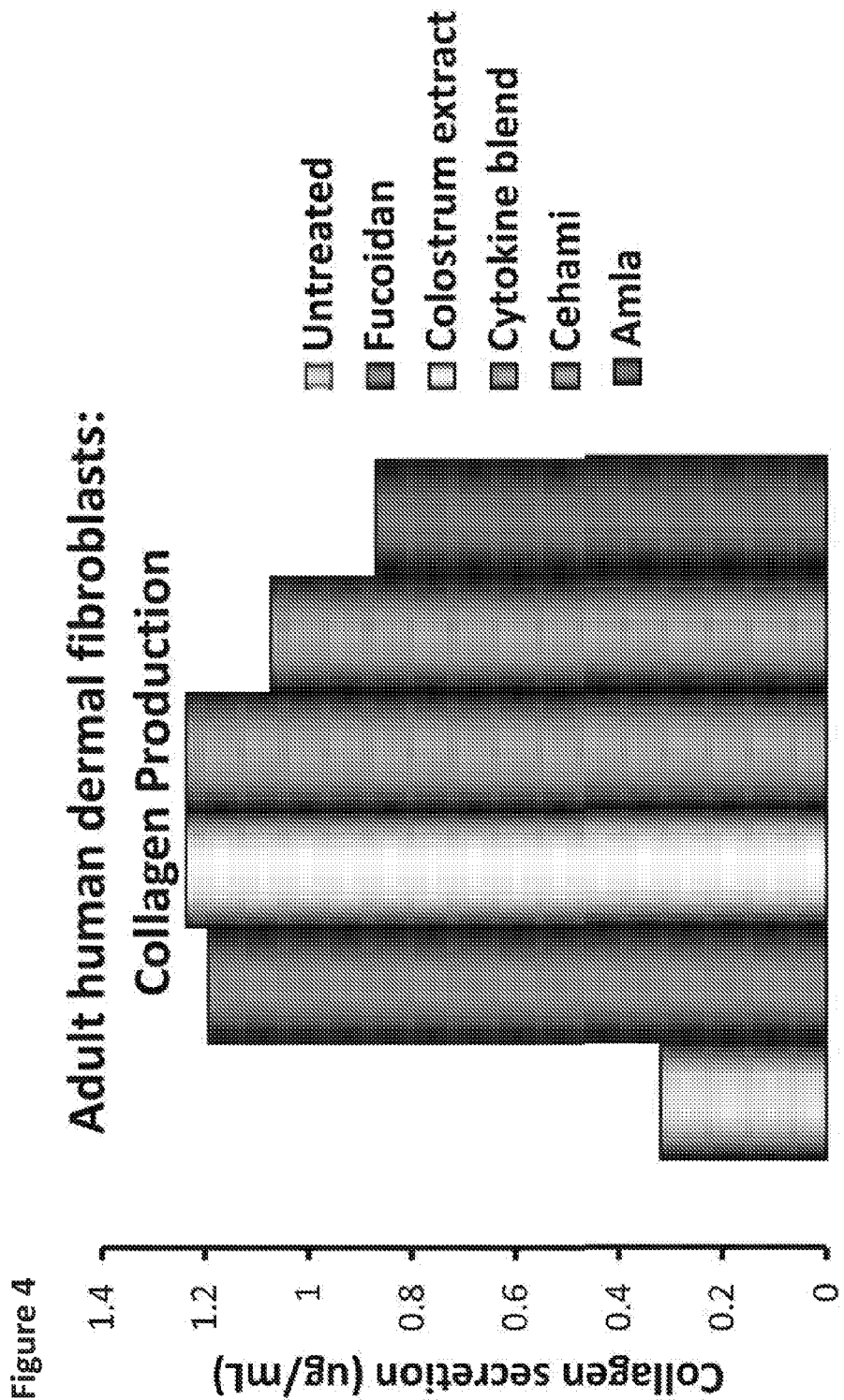
FIG. 4 depicts effects of individual compounds on collagen production. In adult human dermal fibroblasts, collagen production by primary adult human dermal fibroblasts in culture was increased by fucoidan from *Undaria pinnatifida*, bovine colostrum extract, cytokines, cehami (*Centipeda cunninghamii*), and amla (*Phyllanthus emblica*). Whereas control untreated fibroblasts secreted approximately 0.3 μg/mL of collagen, treated samples secreted amounts ranging from 0.8 to over 1.2 μg/mL of collagen.

As shown in FIG. 3, when blended together some of these ingredients showed a significant level of synergy in enhancing the proliferation of adult dermal fibroblasts. While AFA enhanced the proliferation of adult dermal fibroblasts by 26%, and aloe, fucoidan and cehami individually reduced proliferation by 37%, 22% and 30%. Importantly, blends of these various ingredients enhanced proliferation by 42% to 86%. The strongest response was seen with blends of AFA, fucoidan and cehami (86%), aloe and fucoidan (74%), aloe, fucoidan, and cehami (71%), fucoidan and cehami (70%), AFA, aloe and fucoidan (70%), and a blend of all four ingredients (63%). Blending of AFA with cacao and vanilla also created a synergy that increased the proliferation adult dermal fibroblasts by 30% and 15%. A vital component of skin, collagen, was also expressed at higher levels, following application of individual ingredients. As shown in FIG. 4, collagen production by primary adult human dermal fibroblasts in culture was increased by fucoidan from *Undaria pinnatifida*, bovine colostrum extract, cytokines, cehami (*Centipeda cunninghamii*), and amla (*Phyllanthus emblica*). Whereas control untreated fibroblasts secreted approximately 0.3 µg/mL of collagen, treated samples secreted amounts ranging from 0.8 to over 1.2 µg/mL of collagen.

Example 4

Figure 5:
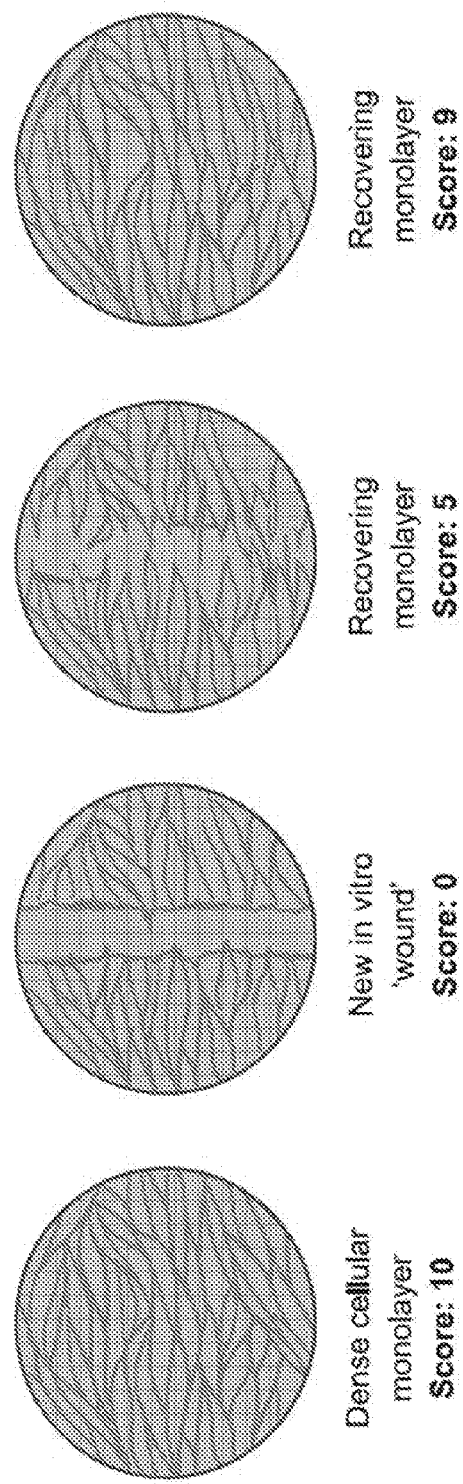
FIG. 5 depicts a wound healing model scratch test. (A): Diagram of an in vitro cellular bioassay model used for wound healing, wherein adult human dermal fibroblasts were cultured until formation of a dense monolayer. A scratch was created through the monolayer, and following treatment with individual compounds, recover was observed after 36 hours. Phenotypic observations with exemplary scoring system ranging from 0-10 is shown. (B): Effect of ingredients on in vitro scratch recovery. A cytokine blend, including epidermal growth factor, fibroblast growth factors, keratinocytes growth factor, hepatocyte growth factors, and stem cell factor, led to a substantial increase in dermal fibroblast migration and accelerated recovery in the in vitro scratch assay. In addition, aloe (*Aloe Barbadensis*), *Aphanizomenon flos-aquae* (AFA), Sangre de drago (*Croton lechleri*), maqui berry (*Aristotelia chilensis*), and bovine colostrum extract supported accelerated recovery.
Figure 5:
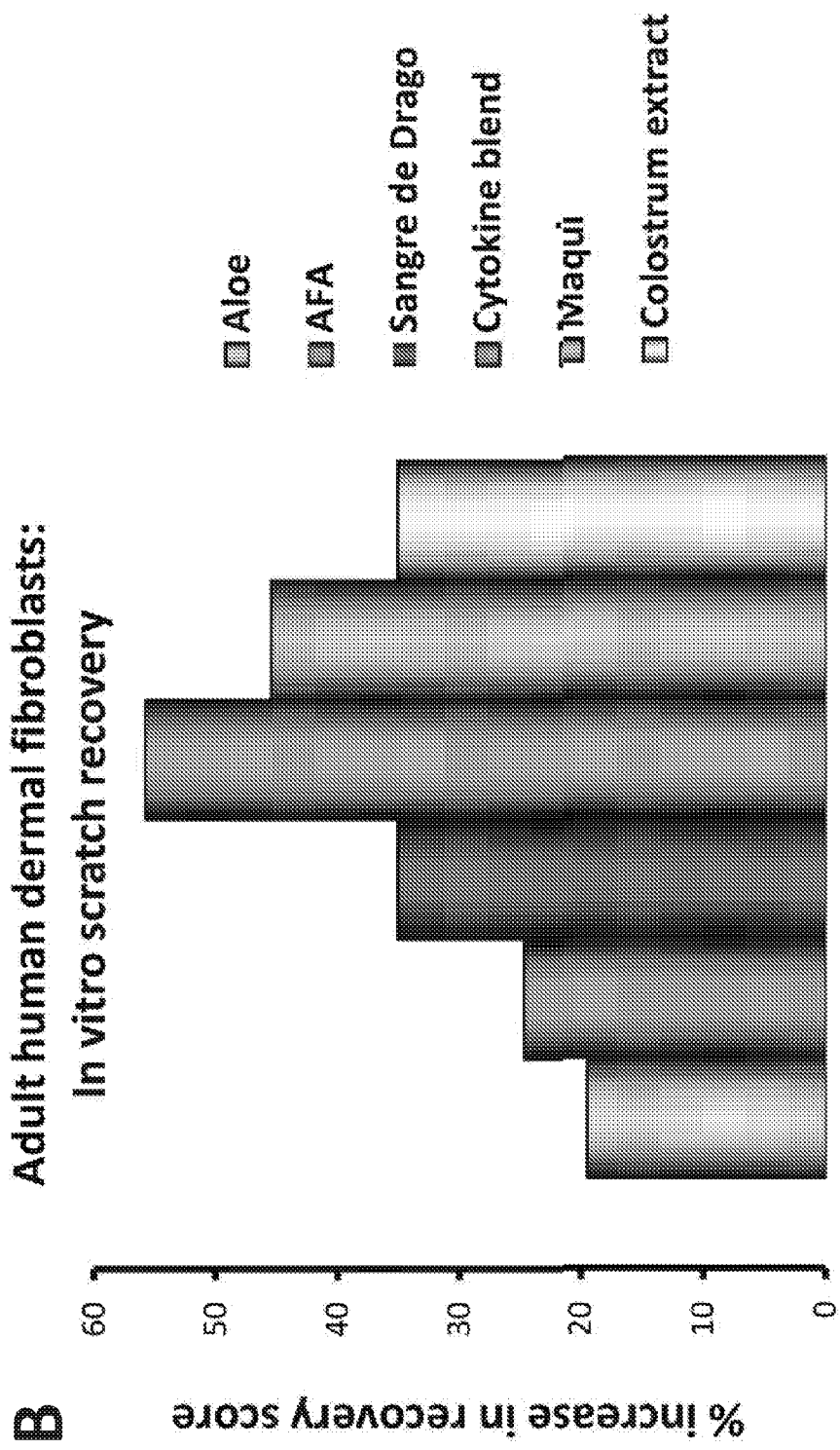
Figure 6:
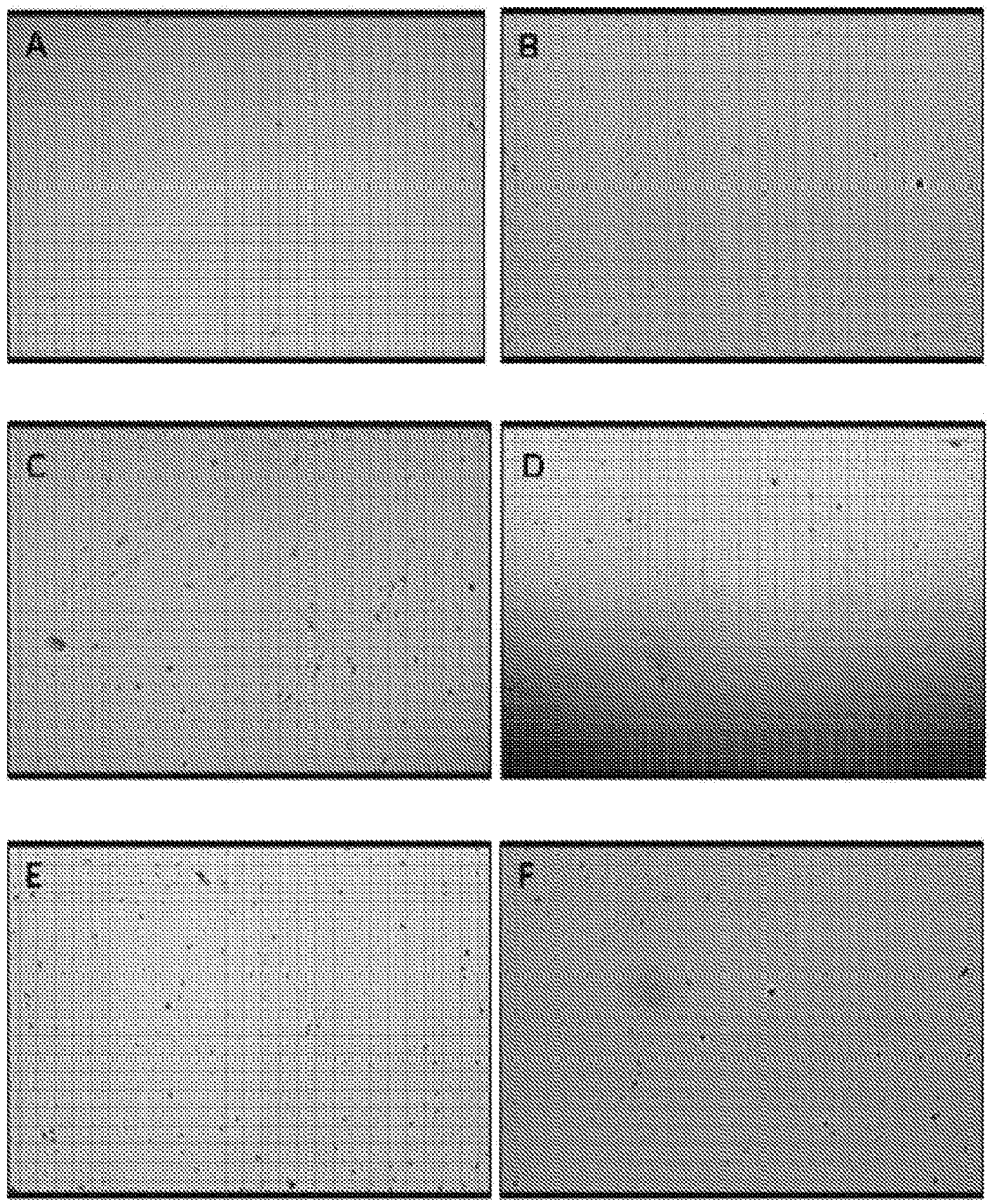
FIG. 6. depicts effect of stem cell proliferation and migration. Neonatal and adult skin fibroblasts grown to confluence in wells were subjected to the scratch test prior to exposure to extracts from various plants in order to study the effect of herbal extracts on stem cell proliferation and migration. Representative results are shown as follows: (A): Control (B): aloe (*Aloe Barbadensis*) (C): black mamaku (*Cyathea medullaris*) (D): *cacao* (*Theobroma cacao*) (E): maqui berry (*Aristotelia chilensis*) (F): berry extracts blend.

Variable Effects of Natural Ingredients in Neonatal and Adult Dermal Fibroblasts As shown in FIG. 5A, an in vitro cellular bioassay wound healing model was applied, wherein adult human dermal fibroblasts were cultured until formation of a dense monolayer, a scratch was created through the monolayer, and following treatment with individual compounds, recovery was observed after 36 hours. Both neonatal and adult skin fibroblasts were grown to confluence in wells and subjected to the scratch test prior to exposure to extracts from various plants in order to study the effect of herbal extracts on stem cell proliferation and migration. Results are shown in Table 1 and FIG. 6. AFA, aloe, fucoidan, cehami, black mamaku, berries, cacao and green tea all significantly enhanced stem cell proliferation and migration. Vanilla, pomegranate and *Croton lechleri* showed moderate effect. Application of a scoring system, as shown in FIG. 5B, demonstrated that a variety of individual ingredients contained significant wound healing properties, with individual ingredients providing an improvement ranging from 20% up to nearly 60% scratch recovery compared to untreated controls.

TABLE 1

Effect of Different Natural Ingredients on Proliferation and Migration

| | Neonatal dermal fibroblasts | | Adult dermal fibroblasts | |
|---|---|---|---|---|
| | Proliferation | migration | Proliferation | migration |
| AFA | ++++ | +++ | ++++ | ++ |
| Aloe | ++++ | +++ | ++++ | ++ |

TABLE 1-continued

Effect of Different Natural Ingredients on Proliferation and Migration

| | Neonatal dermal fibroblasts | | Adult dermal fibroblasts | |
|---|---|---|---|---|
| | Proliferation | migration | Proliferation | migration |
| Fucoidan | ++++ | 0 | ++++ | 0 |
| Black mamaku | + | + | ++++ | — |
| Cehami | ++ | + | +++ | — |
| Pomegranate | ++ | + | 0 | 0 |
| Croton lechleri | + | ++ | 0 | 0 |
| Berries* | ++++ | +++ | +++ | ++ |
| Cacao | +++ | +++ | 0 | ++ |
| Maqui | +++ | ++ | +++ | 0 |
| Green Tea (PE) | 0 | + | ++ | +++ |
| Vanilla Burboun | ++ | 0 | 0 | ++ |

*Wild Bilberry, Wild Ligonberry, Black Currant, Aronia, Pomegranate, Wild Blueberry, Concorde Grape, Sour Cherry, Wild Elderberry, Wild Cranberry, Red Raspberry, Black Raspberry Example 5

Figure 8:
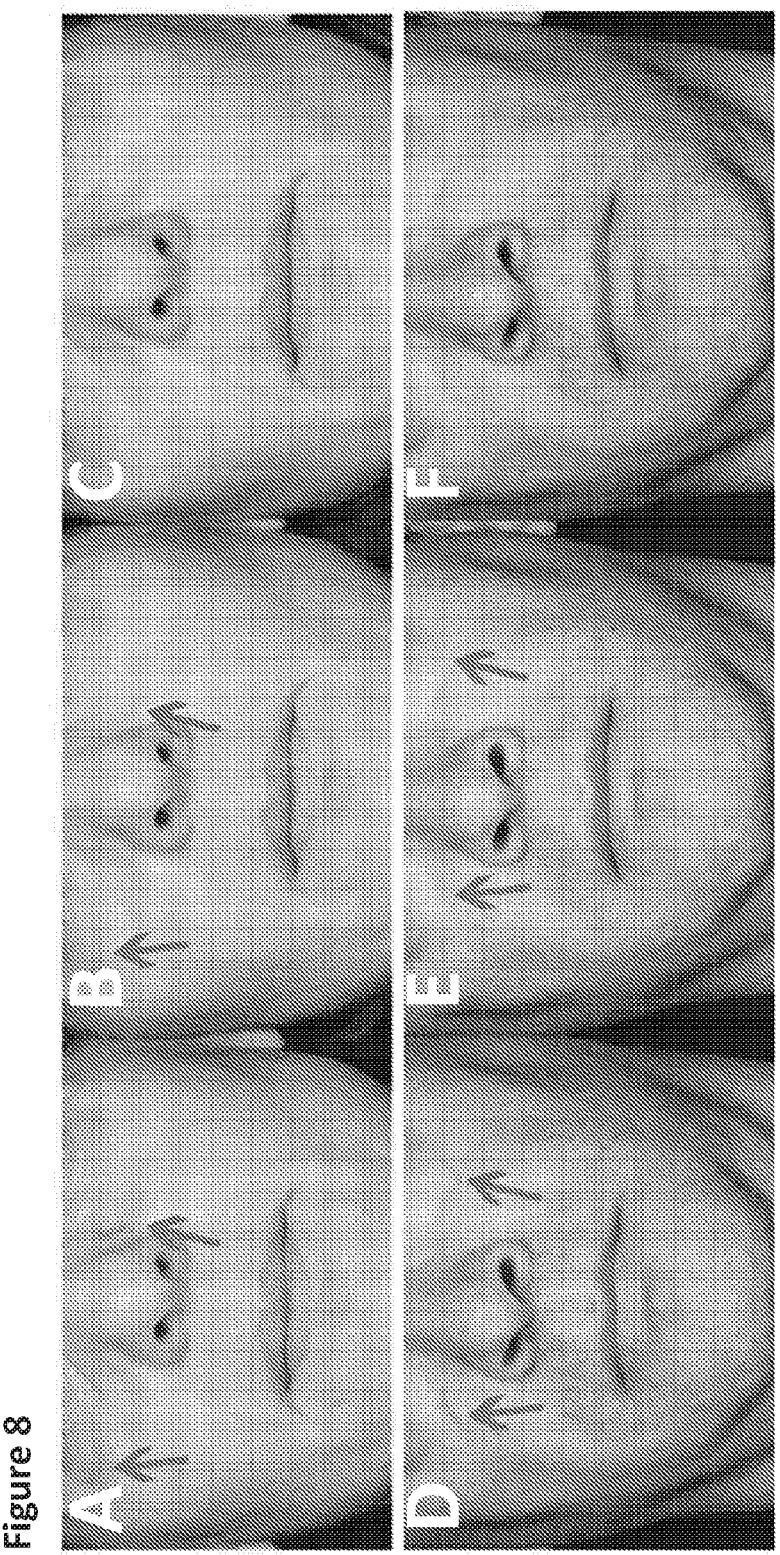
FIG. 8. depicts examples of improvements in skin appearance. Skin appearance is improved following 28 day application of combined ingredients, as shown by wrinkle depth, darkness under eyes, and skin hydration, indicated by red arrows. In open-label study, 10 individuals (5 males and 5 females) used combination of ingredients twice daily for 28 days. Measurements of skin elasticity and moisture, along with surface skin analysis, were performed at 0, 7, 14, and 28 days. A first representative patient example is shown in (A): 0 days, (B): 7 days, and (C): 28 days of treatment. A second representative example is shown in (D): 0 days, (E): 7 days, and (F): 28 days of treatment.

Effective Anti-Wrinkle Results Via Topical Application of a Composition Containing a Combination of Natural Ingredients A combination of natural ingredients was tested over 7, 14, and 28 day periods for conditioning of skin and wrinkle reduction. This combination, provided in a serum containing Coconut oil, Nilotica butter, *Rosa* mosqueta, Olivem 1000, Cocoa butter, Soy lecithin, Chilean Soapnut, NovHyal, Fucoidan Maritech, *Moringa, Aloe* vera, Genistein, Black mamaku, Cehami, Amla, AFA, Pomegranate, Sangre de drago, Guar, *Vanilla*, Colostrum, Cytokines, Maqui, Synergy berries, Green Tea Extract, *Vanilla* 20 fold extract, Cacao, Olive extract (Hydroxytyrolosol), Vitamin E (Sunflower), Samambaia, Bulgarian Rose, Jasmine, Sweet Orange, Ylang-ylang, Tangerine Essential Oil, Bitter Orange extract, and Honeysuckle, demonstrated effective results following both short term (e.g., 7 day) and longer term (e.g., 28 day application). For example, application of the serum over a short 7 day period resulted in a 74% wrinkle reduction as shown by the representative individual depicted in FIG. 7A, and an 81% wrinkle reduction by the individual shown in FIG. 7B, as measured across the entirety of the individual's facial features. Common areas where wrinkles are pronounced, such as the base of the eyelids and forehead, similarly benefited from application of the serum. For example, as depicted in FIG. 8, skin appearance is improved following 28 day application of combined ingredients, when using a combination of ingredients twice daily for 28 days. In another representative example using Visioscan imaging, as depicted in FIG. 7A, 28 day application led to an 82% reduction in wrinkles located near the base of the lower eyelid. A similarly remarkable reduction of about 75% was observed on the forehead, as depicted in FIG. 7B.

Figure 10:
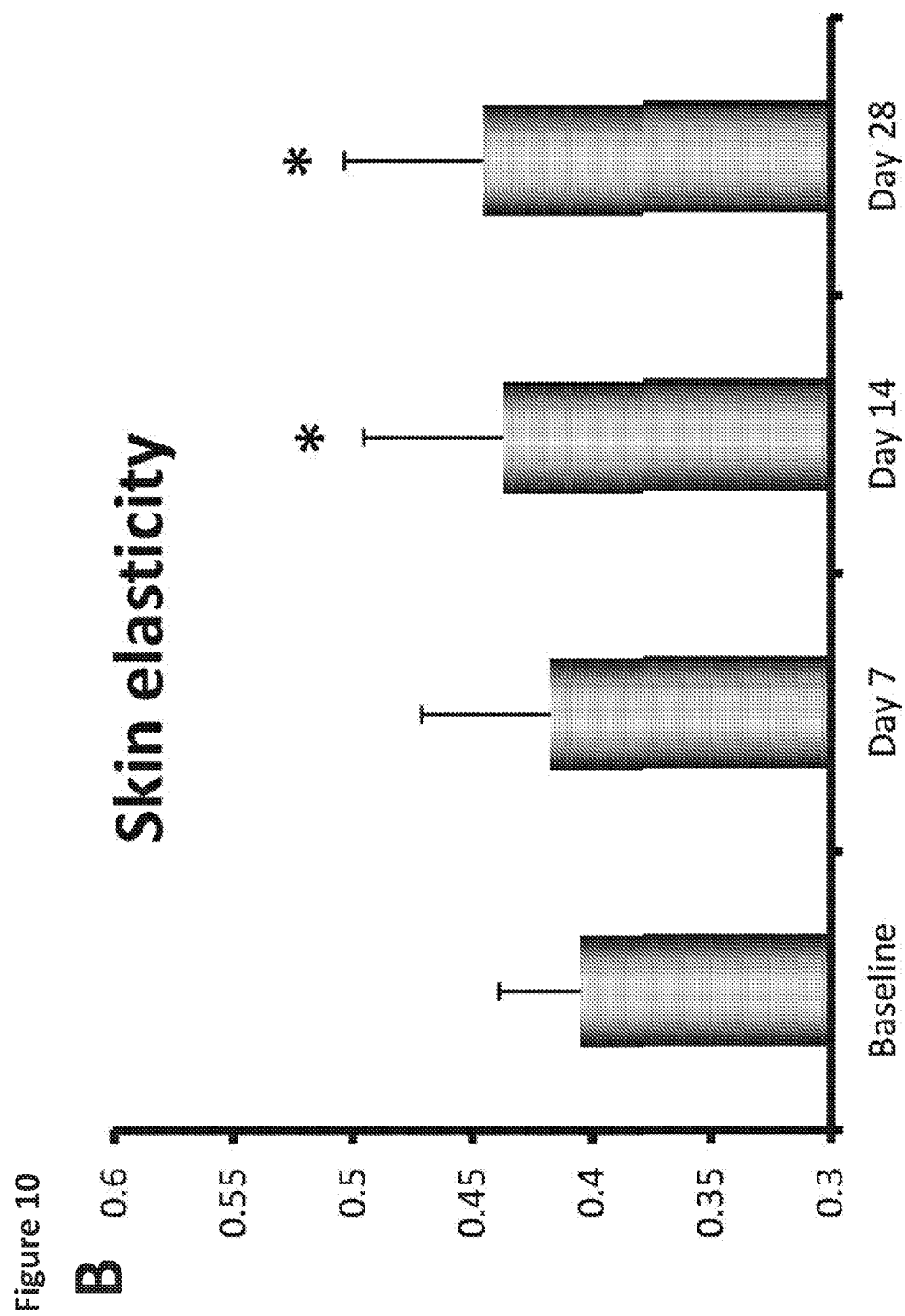
FIG. 10. depicts measurements of skin properties. (A): Visioscan image analysis system was deployed to image wrinkle appearance as associated with surface roughness from fine and coarse wrinkle depth. Combinations of ingredients applied over a 28-day period demonstrated dramatic decreases in surface roughness, with highly significant decreases appearing at 7 days (* indicating statistical significance, $p<0.001$), and remained highly significant at 14 and 28 days of product use (* indicating statistical significance, $p<0.02$). Average reductions were 9.8%, 17.4%, and 25.3% after 7, 14, and 28 days of use, respectively, with maximum % improvement reaching 39.3%. (B): Evaluation of skin elasticity/flexibility via cutometer indicated an increase in biological elasticity on the test sites treated with the test product. The increases were statistically significant from baseline after 14 and 28 days of use (as indicated by *), and averaged a 10% increase in elasticity, with maximum % improvement reaching 31.9%. (C): Nova Dermal Phase meter was deployed for skin hydration measurement. Measurements demonstrated that the test product dramatically increase the skin moisture content. The increases were statistically significant from baseline after 14 and 28 days of use (as indicated by *) with average increases of 29.7% and 30.5%.
Figure 10:
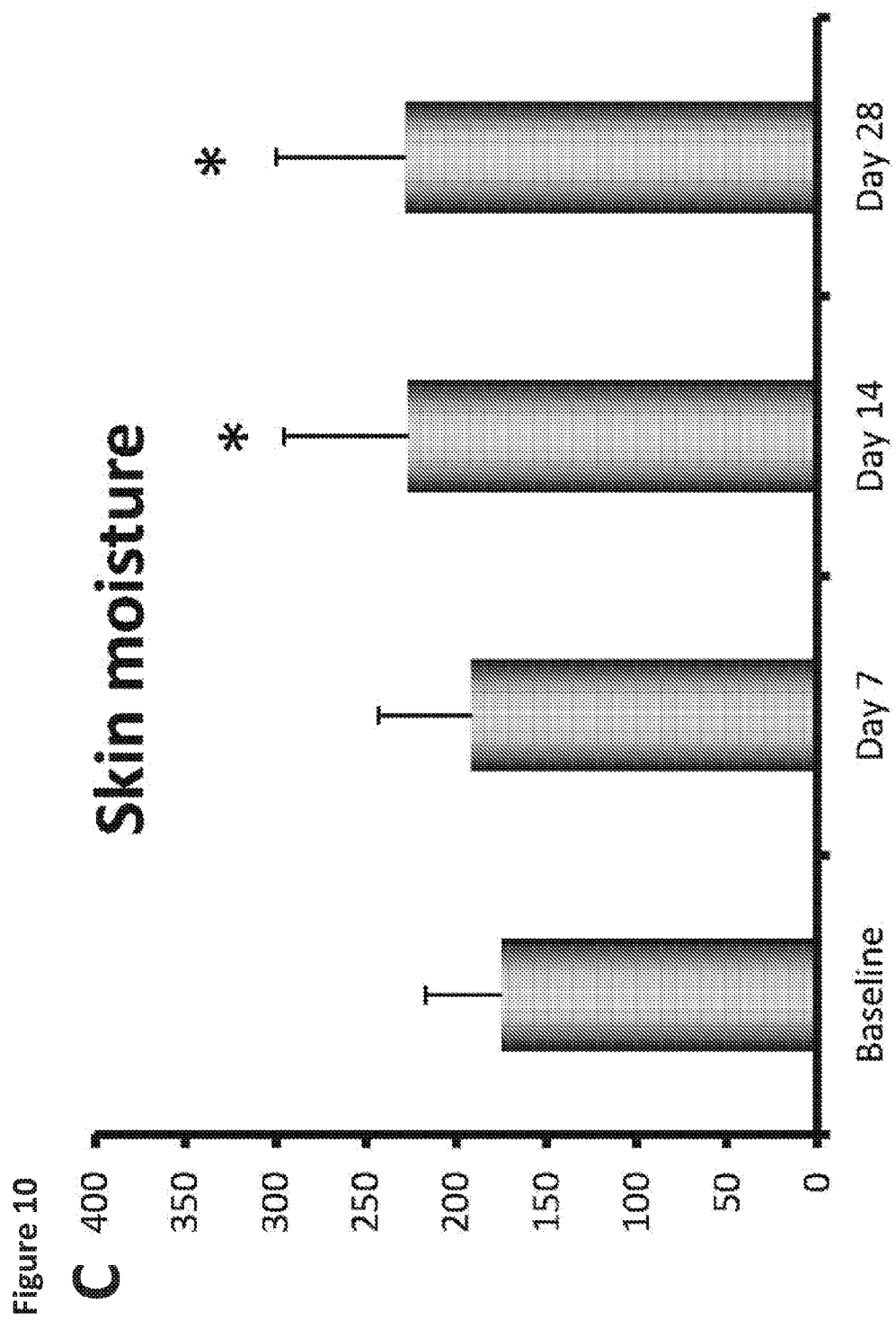

Wrinkle reduction was further correlated to a variety of improved aesthetic features, including moisture retention and improved skin elasticity. These improvements were measurable and statistically significant. For example, FIG. 10A depicts measurements of skin properties. Visioscan image analysis system showed that combinations of ingredients applied over a 28-day period demonstrated dramatic decreases in surface roughness, with highly significant decreases appearing at 7 days (* indicating statistical significance, $p<0.001$), and remained highly significant at 14 and 28 days of product use (* indicating statistical significance, $p<0.02$). Average reductions were 9.8%, 17.4%, and 25.3% after 7, 14, and 28 days of use, respectively, with maximum % improvement reaching 39.3%. Likewise, FIG. 10B demonstrates that measurement of skin elasticity/flexibility via cutometer indicated an increase in biological elasticity on the test sites treated with the test product. The increases were statistically significant from baseline after 14 and 28 days of use (as indicated by *), and averaged a 10% increase in elasticity, with maximum % improvement reaching 31.9%. Similarly, FIG. 10C shows that when using Nova Dermal Phase meter for skin hydration measurement, combinations of ingredients dramatically increase the skin moisture content. The increases were statistically significant from baseline after 14 and 28 days of use (as indicated by *) with average increases of 29.7% and 30.5%.

Figure 11:
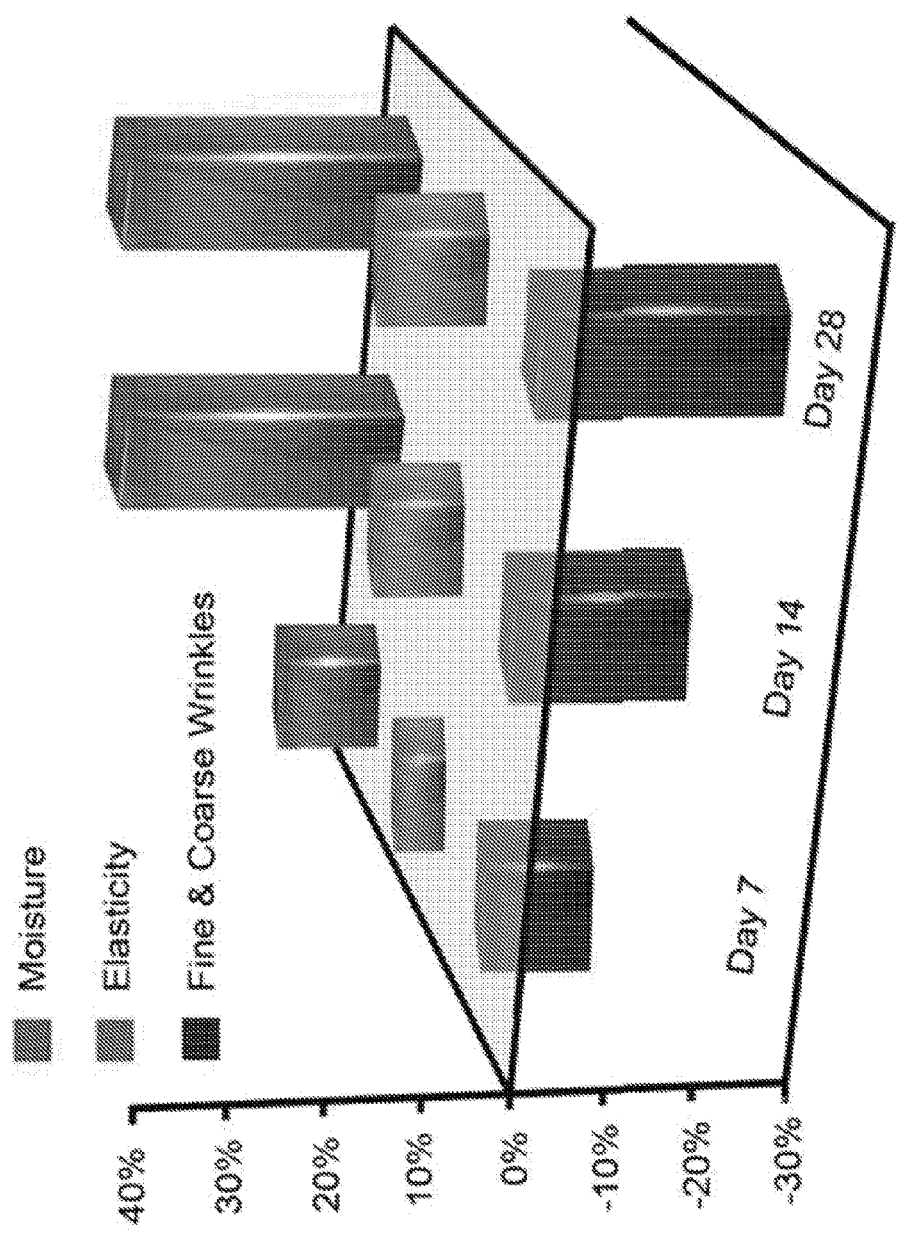
FIG. 11. depicts improvements in moisture retention, elasticity and wrinkle removal. Topical application of a serum containing cold infused extracts of *Aphanizomenon flos-aquae* (AFA), fucoidan from *Undaria pinnatifida*, aloe (*Aloe Barbadensis*), cehami (*Centipeda cunninghamii*), black mamaku (*Cyathea medullaris*), cacao (*Theobroma cacao*), berry extracts blend, maqui berry (*Aristotelia chilensis*), colostrum, vanilla (*Vanilla planifolia*), pomegranate (*Punica granatum*), Sangre de drago (*Croton lechleri*), and green tea (*Camellia sinensis*) led to a 25% reduction in wrinkle, 30% increase in moisture retention and 10% increase in elasticity. Results across 7-day, 14-day and 28-day time periods clearly demonstrate an improvement over time.

In an additional example demonstrating the results of these features together, FIG. 11 shows that following serum application over 7, 14, and 28 day periods, measurements indicated up to a 25% reduction in wrinkles, up to a 30% increase in moisture retention and up to a 10% increase in elasticity.

Example 6

Biochemical Activity of Combined Ingredients Affecting Improved Skin Appearance

Figure 12:
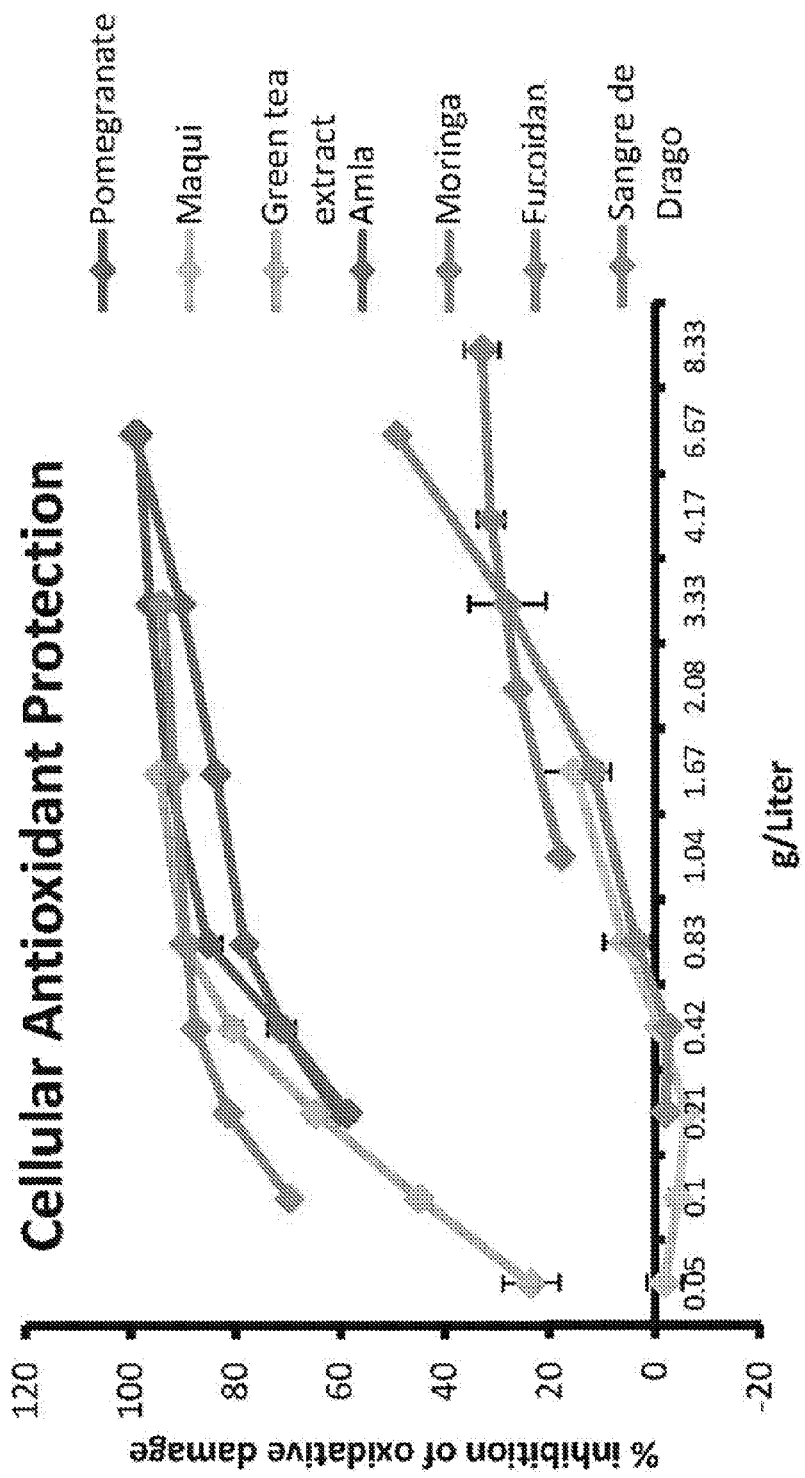
FIG. 12. depicts effects of individual compounds on cellular antioxidant protection. Cellular antioxidant protection capacity of each ingredient was tested in the CAP-e bioassay. The in vitro data demonstrated potent antioxidant bioavailability by amla (*Phyllanthus emblica*), pomegranate (*Punica granatum*), Sangre de drago (*Croton lechleri*), and green tea (*Camellia sinensis*).

Without being bound by any particular theory, it is suggested that the improved appearance of skin results from minimizing biochemical activity associated with skin aging. Two well-known factors influencing skin aging including the insults associated with oxidation, and damage caused by free radical exposure. To characterize the effects of individual compounds on these key biochemical processes, the inventors investigated the effects of individual compounds on cellular antioxidant protection using CAP-e bioassay. As shown in FIG. 12, the in vitro data demonstrated potent antioxidant bioavailability by amla (*Phyllanthus emblica*), pomegranate (*Punica granatum*), Sangre de drago (*Croton lechleri*), and green tea (*Camellia sinensis*). At higher concentrations, nearly all tested compounds exhibited inhibitory activity of oxidative damage. Most notably, amla (*Phyllanthus emblica*), pomegranate (*Punica granatum*), and Sangre de drago (*Croton lechleri*), all showed potent inhibitory activity, even with concentrations as low as 0.21 g/L.

Figure 13:
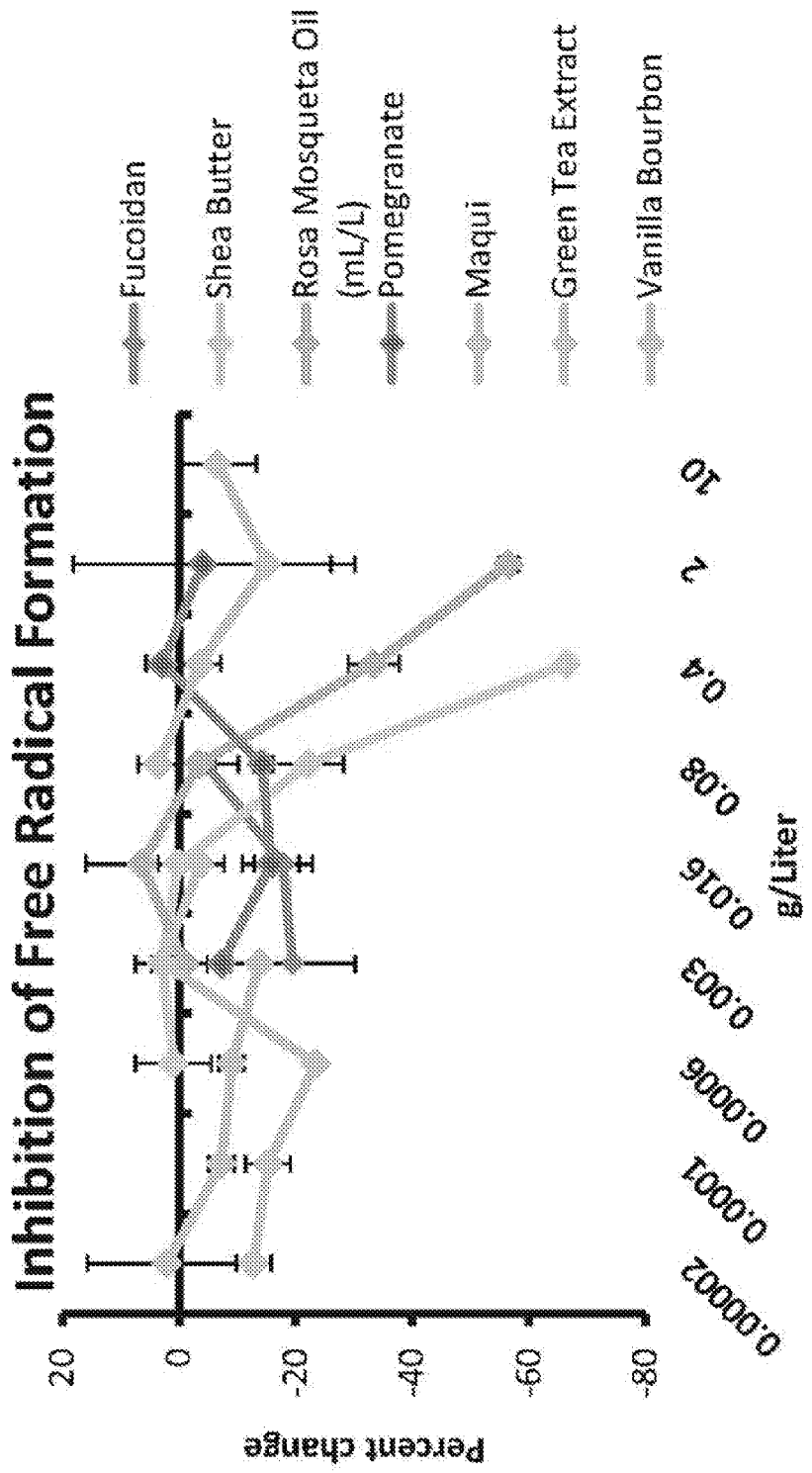
FIG. 13. depicts effects of individual compounds on inhibiting free radical formation. The inhibitory effect of each ingredient on free radical formation by inflammatory cells placed under oxidative stress conditions was tested. The in vitro data demonstrated reduced free radical production by individual compounds, including fucoidan from *Undaria pinnatifida*, Shea butter, rosa mosqueta (*Rosa rubiginosa*), maqui berry (*Aristotelia chilensis*), vanilla (*Vanilla planifolia*), and green tea (*Camellia sinensis*).

Similarly, the inventors observed individual compounds inhibiting free radical formation, as shown in FIG. 13. The inhibitory effect of each ingredient on free radical formation by inflammatory cells placed under oxidative stress conditions was tested. The in vitro data demonstrated reduced free radical production by individual compounds, including fucoidan from *Undaria pinnatifida*, Shea butter, rosa mosqueta (*Rosa rubiginosa*), maqui berry (*Aristotelia chilensis*), vanilla (*Vanilla planifolia*), and green tea (*Camellia sinensis*). Various concentrations of individual compounds demonstrated pronounced reduction of up to 70% of free radical formation.

Example 7

Compositions Containing Different Combinations of Natural Ingredients

As shown as examples in Tables 2-6, different combinations of natural ingredients may be added together to vary the contents of a compositions for a skin care conditioning product. Table 2 provides general examples, with specific compositions compatible with the present invention being described in Tables 3-6. Across various compositions, the combinations of ingredient should constitute approximately about 12-15% of the final composition volume, as shown across the various examples.

TABLE 2

Various Examples of Variable Amounts of Natural Ingredients in Different Compositions

| Ingredients | INCI | % (w/w) | g-ml/ 50 ml | Form | Part used |
|---|---|---|---|---|---|
| Coconut oil | Cocos Nucifera | 0-10% | 0-5.0 | oil | endosperm/ fruit |
| Nilotica butter | Vitellaria nilotica | 0-3.6% | 0-1.8 | butter | nut |
| Rosa mosqueta | Rosa Rubiginosa | 0-3.6% | 0-1.8 | oil | fruit |
| Olivem 1000 | Ceteryl Olivate | 0-6.0% | 0-3.0 | oil | fruit |
| Cocoa butter | Theobroma cacao | 0-3.6% | 0-1.8 | butter | bean |
| Soy lecithin | Glycine Max | 0-1.6% | 0-0.8 | oil | bean |
| Chilean Soapnut | Quillaja Saponaria | 0-3.0% | 0-1.5 | Syrup | bark |
| NovHyal | NAG6P | 0-4.0% | 0-2.0 | Aqueous | biotech |
| Fucoidan Maritech | Laminaria Japonica | 0-3.0% | 0-1.5 | Powder | whole plant |
| Moringa | Moringa Oleifera | 0-3.0% | 0-1.5 | Powder | leaf |
| Aloe vera | Aloe Barbadensis | 0-2.0% | 0-1.0 | Powder | leaf (gel) |
| Genistein | soy | 0-1.33% | 0-0.66 | Powder | bean |
| Black mamaku | Cyathea Medularis | 0-1.33% | 0-0.66 | Powder | frond |
| Cehami | Centipeda Cunninghamii | 0-1.33% | 0-0.66 | Powder | leaves |
| Amla | Phyllanthus emblica | 0-1.33% | 0-0.66 | Powder | fruit |
| AFA | Aphanizomenon flosaquae | 0-0.66% | 0-0.33 | Powder | whole plant |
| Pomegranate | Punica Granatum | 0-0.66% | 0-0.33 | Powder | fruit |
| Sangre de drago | Croton lechleri | 0-0.66% | 0-0.33 | Powder | sap |
| Guar | Cyamopsis tetragonolobus | 0-1.33% | 0-0.66 | Powder | seed |
| Vanilla | Vanilla planifolia | 0-1.33% | 0-0.66 | Powder | bean |
| Colostrum | first milk | 0-0.66% | 0-0.33 | Powder | milk |
| Cytokines* | E. coli | 0-0.20%** | 0-0.10 | Aqueous | cultures |
| Maqui | Aristotelia Chilensis | 0-0.50% | 0-0.25 | Powder | berries |
| Synergy berries± | 12 berries | 0-0.50% | 0-0.25 | Powder | berries |
| Green Tea Extract | Camellia sinensis | 0-0.50% | 0-0.25 | Powder | leaf |
| Vanilla 20 fold extract | Vanilla planifolia | 0-0.44% | 0-0.22 | Powder | bean |
| Cacao | Theobroma Cacao | 0-0.4% | 0-0.20 | Powder | bean |
| Olive extract (Hydroxytyrolosol) | Olea europaea | 0-2.0% | 0-1.0 | Powder | fruit |
| Vitamin E (Sunflower) | Helianthus annuus | 0-1.6% | 0-0.80 | oil | seed |
| Samambaia | Polypodium leucotomos | 0-1.0% | 0-0.50 | Powder | leaf |
| Bulgarian Rose | Rosa Damascena | 0-0.44% | 0-0.22 | oil | flower |
| Jasmine | Jasminum Grandis locum | 0-0.48% | 0-0.24 | oil | flower |
| Sweet Orange | Citrus Sinensis | 0-0.80% | 0-0.40 | oil | peel |
| Ylang-ylang | Cananga Odorata | 0-0.24% | 0-0.12 | oil | flower |
| Tangerine Essential Oil | Citrus Reticulata | 0-0.02% | 0.01 | oil | peel |
| Bitter Orange extract | Citrus aurantium | 0-2.5% | 0-1.25 | Aqueous | seed |
| Honeysuckle | Lonicera Japonica | 0-2.5% | 0-1.25 | Aqueous | flower |

*aFGF, bFGF, KGF2, VEGF, SCF 1/3
**varies depending on stock concentration. For example a 0.2% concentration assumes 50 ppm stock solution.
±Wild Bilberry, Wild Ligonberry, Black Currant, Aronia, Pomegranate, Wild Blueberry, Concorde Grape, Sour Cherry, Wild Elderberry, Wild Cranberry, Red Raspberry, Black Raspberry

TABLE 3

Specific Example of Natural Ingredients for a Serum Composition

| Ingredients | INCI | % (w/w) | g-ml/ 50 ml | Form | Part used |
|---|---|---|---|---|---|
| Coconut oil | Cocos Nucifera | 5.0% | 2.5 | oil | endosperm/ fruit |
| Nilotica butter | Vitellaria nilotica | 2.0% | 1.0 | butter | nut |
| Rosa mosqueta | Rosa Rubiginosa | 1.8% | 0.9 | oil | fruit |
| Olivem 1000 | Ceteryl Olivate | 3.0% | 1.5 | oil | fruit |
| Cocoa butter | Theobroma cacao | 1.8% | 0.9 | butter | bean |
| Soy lecithin | Glycine Max | 0.80% | 0.4 | oil | bean |
| Chilean Soapnut | Quillaja Saponaria | 1.5% | 0.75 | Syrup | bark |
| NovHyal | NAG6P | 1.8% | .9 | Aqueous | biotech |

TABLE 3-continued

Specific Example of Natural Ingredients for a Serum Composition

| Ingredients | INCI | % (w/w) | g-ml/ 50 ml | Form | Part used |
|---|---|---|---|---|---|
| Fucoidan Maritech | *Laminaria Japonica* | 2.0% | 1 | Powder | whole plant |
| Moringa | *Moringa Oleifera* | 1.0% | 0.5 | Powder | leaf |
| Aloe vera | *Aloe Barbadensis* | 1.0% | 0.5 | Powder | leaf (gel) |
| Genistein | soy | 0.66% | 0.33 | Powder | bean |
| Black mamaku | *Cyathea Medularis* | 0.33% | 0.165 | Powder | frond |
| Cehami | *Centipeda Cunninghamii* | 0.33% | 0.165 | Powder | leaves |
| Amla | *Phyllanthus emblica* | 0.33% | 0.165 | Powder | fruit |
| AFA | *Aphanizomenon flos-aquae* | 0.33% | 0.165 | Powder | whole plant |
| Pomegranate | *Punica Granatum* | 0.33% | 0.165 | Powder | fruit |
| Sangre de drago | *Croton lechleri* | 0.33% | 0.165 | Powder | sap |
| Guar | *Cyamopsis tetragonolobus* | 0.66% | 0.33 | Powder | seed |
| Vanilla | *Vanilla planifolia* | 0.66% | 0.33 | Powder | bean |
| Colostrum | first milk | 0.33% | 0.165 | Powder | milk |
| Cytokines | *E. coli* | 0.10% | 0.05 | Aqueous | cultures |
| Maqui | *Aristotelia Chilensis* | 0.25% | 0.125 | Powder | berries |
| Synergy berries | 12 berries | 0.25% | 0.125 | Powder | berries |
| Green Tea Extract | *Camellia sinensis* | 0.25% | 0.125 | Powder | leaf |
| Vanilla 20 fold extract | *Vanilla planifolia* | 0.22% | 0.11 | Powder | bean |
| Cacao | *Theobroma Cacao* | 0.20% | 0.1 | Powder | bean |
| Olive extract (Hydroxytyrolosol) | *Olea europaea* | 2.0% | 1.0 | Powder | fruit |
| Vitamin E (Sunflower) | *Helianthus annuus* | 0.8% | 0.4 | oil | seed |
| Samambaia | *Polypodium leucotomos* | 0.5% | 0.25 | Powder | leaf |
| Bulgarian Rose | *Rosa Damascena* | 0.22% | 0.11 | oil | flower |
| Jasmine | *Jasminum Grandiflorum* | 0.24% | 0.12 | oil | flower |
| Sweet Orange | *Citrus Sinensis* | 0.40% | 0.2 | oil | peel |
| Ylang-ylang | *Cananga Odorata* | 0.12% | 0.06 | oil | flower |
| Tangerine Essential Oil | *Citrus Reticulata* | 0.01% | 0.005 | oil | peel |
| Bitter Orange extract | *Citrus aurantium* | 1.25% | 0.625 | Aqueous | seed |
| Honeysuckle | *Lonicera Japonica* | 1.25% | 0.625 | Aqueous | flower |

TABLE 4

Specific Example of Natural Ingredients for a Serum Composition

| Ingredients | INCI | % (w/w) | g-ml/ 50 ml | Form | Part used |
|---|---|---|---|---|---|
| Coconut oil | *Cocos Nucifera* | 5.0% | 2.5 | oil | endosperm/fruit |
| Nilotica butter | *Vitellaria nilotica* | 1.8% | 0.9 | butter | nut |
| Rosa mosqueta | *Rosa Rubiginosa* | 1.8% | 0.9 | oil | fruit |
| Olivem 1000 | *Ceteryl Olivate* | 3.0% | 1.5 | oil | fruit |
| Cocoa butter | *Theobroma cacao* | 1.8% | 0.9 | butter | bean |
| Soy lecithin | *Glycine Max* | 0.80% | 0.4 | oil | bean |
| Chilean Soapnut | *Quillaja Saponaria* | 1.5% | 0.75 | Syrup | bark |
| NovHyal | NAG6P | 2.0% | 1 | Aqueous | biotech |
| Fucoidan Maritech | *Laminaria Japonica* | 1.5% | 0.75 | Powder | whole plant |
| Moringa | *Moringa Oleifera* | 1.50% | 0.75 | Powder | leaf |
| Aloe vera | *Aloe Barbadensis* | 1.0% | 0.5 | Powder | leaf (gel) |
| Genistein | soy | 0.66% | 0.33 | Powder | bean |
| Black mamaku | *Cyathea Medularis* | 0.66% | 0.33 | Powder | frond |
| Cehami | *Centipeda Cunninghamii* | 0.66% | 0.33 | Powder | leaves |
| Amla | *Phyllanthus emblica* | 0.66% | 0.33 | Powder | fruit |
| AFA | *Aphanizomenon flos-aquae* | 0.33% | 0.165 | Powder | whole plant |
| Pomegranate | *Punica Granatum* | 0.33% | 0.165 | Powder | fruit |
| Sangre de drago | *Croton lechleri* | 0.33% | 0.165 | Powder | sap |
| Guar | *Cyamopsis tetragonolobus* | 0.66% | 0.33 | Powder | seed |
| Vanilla | *Vanilla planifolia* | 0.66% | 0.33 | Powder | bean |
| Colostrum | first milk | 0.33% | 0.165 | Powder | milk |
| Cytokines | *E. coli* | 0.10% | 0.05 | Aqueous | cultures |
| Maqui | *Aristotelia Chilensis* | 0.25% | 0.125 | Powder | berries |
| Synergy berries | 12 berries | 0.25% | 0.125 | Powder | berries |
| Green Tea Extract | *Camellia sinensis* | 0.25% | 0.125 | Powder | leaf |
| Vanilla 20 fold extract | *Vanilla planifolia* | 0.22% | 0.11 | Powder | bean |
| Cacao | *Theobroma Cacao* | 0.20% | 0.1 | Powder | bean |
| Olive extract (Hydroxytyrolosol) | *Olea europaea* | 1.0% | 0.5 | Powder | fruit |
| Vitamin E (Sunflower) | *Helianthus annuus* | 0.8% | 0.4 | oil | seed |
| Samambaia | *Polypodium leucotomos* | 0.5% | 0.25 | Powder | leaf |
| Bulgarian Rose | *Rosa Damascena* | 0.22% | 0.11 | oil | flower |
| Jasmine | *Jasminum Grandiflorum* | 0.24% | 0.12 | oil | flower |

TABLE 4-continued

Specific Example of Natural Ingredients for a Serum Composition

| Ingredients | INCI | % (w/w) | g-ml/ 50 ml | Form | Part used |
|---|---|---|---|---|---|
| Sweet Orange | *Citrus Sinensis* | 0.40% | 0.2 | oil | peel |
| Ylang-ylang | *Cananga Odorata* | 0.12% | 0.06 | oil | flower |
| Tangerine Essential Oil | *Citrus Reticulata* | 0.01% | 0.005 | oil | peel |
| Bitter Orange extract | *Citrus aurantium* | 1.25% | 0.625 | Aqueous | seed |
| Honeysuckle | *Lonicera Japonica* | 1.25% | 0.625 | Aqueous | flower |

TABLE 5

Specific Example of Natural Ingredients for a Serum Composition

| Ingredients | INCI | % (w/w) | g-ml/ 50 ml | Form | Part used |
|---|---|---|---|---|---|
| Coconut oil | *Cocos Nucifera* | 5.0% | 2.5 | oil | endosperm/fruit |
| Nilotica butter | *Vitellaria nilotica* | 1.8% | 0.9 | butter | nut |
| Rosa mosqueta | *Rosa Rubiginosa* | 1.3% | 0.65 | oil | fruit |
| Olivem 1000 | *Ceteryl Olivate* | 3.0% | 1.5 | oil | fruit |
| Cocoa butter | *Theobroma cacao* | 1.8% | 0.9 | butter | bean |
| Soy lecithin | *Glycine Max* | 0.80% | 0.4 | oil | bean |
| Chilean Soapnut | *Quillaja Saponaria* | 2.0% | 1.0 | Syrup | bark |
| NovHyal | NAG6P | 2.0% | 1.0 | Aqueous | biotech |
| Fucoidan Maritech | *Laminaria Japonica* | 0.5% | 0.25 | Powder | whole plant |
| Moringa | *Moringa Oleifera* | 2.0% | 1.0 | Powder | leaf |
| Aloe vera | *Aloe Barbadensis* | 0.5% | 0.25 | Powder | leaf (gel) |
| Genistein | soy | 0.66% | 0.33 | Powder | bean |
| Black mamaku | *Cyathea Medularis* | 0.66% | 0.33 | Powder | frond |
| Cehami | *Centipeda Cunninghamii* | 0.66% | 0.33 | Powder | leaves |
| Amla | *Phyllanthus emblica* | 0.66% | 0.33 | Powder | fruit |
| AFA | *Aphanizomenon flos-aquae* | 0.66% | 0.33 | Powder | whole plant |
| Pomegranate | *Punica Granatum* | 0.66% | 0.33 | Powder | fruit |
| Sangre de drago | *Croton lechleri* | 0.66% | 0.33 | Powder | sap |
| Guar | *Cyamopsis tetragonolobus* | 0.66% | 0.33 | Powder | seed |
| Vanilla | *Vanilla planifolia* | 0.66% | 0.33 | Powder | bean |
| Colostrum | first milk | 0.33% | 0.165 | Powder | milk |
| Cytokines | *E. coli* | 0.10% | 0.05 | Aqueous | cultures |
| Maqui | *Aristotelia Chilensis* | 0.50% | 0.25 | Powder | berries |
| Synergy berries | 12 berries | 0.25% | 0.125 | Powder | berries |
| Green Tea Extract | *Camellia sinensis* | 0.25% | 0.125 | Powder | leaf |
| Vanilla 20 fold extract | *Vanilla planifolia* | 0.22% | 0.11 | Powder | bean |
| Cacao | *Theobroma Cacao* | 0.20% | 0.1 | Powder | bean |
| Olive extract (Hydroxytyrolosol) | *Olea europaea* | 1.0% | 0.5 | Powder | fruit |
| Vitamin E (Sunflower) | *Helianthus annuus* | 0.8% | 0.4 | oil | seed |
| Samambaia | *Polypodium leucotomos* | 0.75% | 0.375 | Powder | leaf |
| Bulgarian Rose | *Rosa Damascena* | 0.24% | 0.12 | oil | flower |
| Jasmine | *Jasminum Grandiflorum* | 0.22% | 0.11 | oil | flower |
| Sweet Orange | *Citrus Sinensis* | 0.40% | 0.2 | oil | peel |
| Ylang-ylang | *Cananga Odorata* | 0.12% | 0.06 | oil | flower |
| Tangerine Essential Oil | *Citrus Reticulata* | 0.01% | 0.005 | oil | peel |
| Bitter Orange extract | *Citrus aurantium* | 1.0% | 0.5 | Aqueous | seed |
| Honeysuckle | *Lonicera Japonica* | 1.0% | 0.5 | Aqueous | flower |

TABLE 6

Specific Example of Natural Ingredients for a Serum Composition

| Ingredients | INCI | % (w/w) | g-ml/ 50 ml | Form | Part used |
|---|---|---|---|---|---|
| Coconut oil | *Cocos Nucifera* | 5.0% | 2.5 | oil | endosperm/fruit |
| Nilotica butter | *Vitellaria nilotica* | 2.0% | 1.0 | butter | nut |
| Rosa mosqueta | *Rosa Rubiginosa* | 2.0% | 1.0 | oil | fruit |
| Olivem 1000 | *Ceteryl Olivate* | 3.0% | 1.5 | oil | fruit |
| Cocoa butter | *Theobroma cacao* | 2.0% | 1.0 | butter | bean |
| Soy lecithin | *Glycine Max* | 0.40% | 0.2 | oil | bean |
| Chilean Soapnut | *Quillaja Saponaria* | 1.3% | 0.65 | Syrup | bark |
| NovHyal | NAG6P | 1.5% | 0.75 | Aqueous | biotech |
| Fucoidan Maritech | *Laminaria Japonica* | 2.0% | 1.0 | Powder | whole plant |

TABLE 6-continued

Specific Example of Natural Ingredients for a Serum Composition

| Ingredients | INCI | % (w/w) | g-ml/ 50 ml | Form | Part used |
|---|---|---|---|---|---|
| Moringa | *Moringa Oleifera* | 1.50% | 0.75 | Powder | leaf |
| Aloe vera | *Aloe Barbadensis* | 1.0% | 0.5 | Powder | leaf (gel) |
| Genistein | soy | 0.66% | 0.33 | Powder | bean |
| Black mamaku | *Cyathea Medularis* | 0.66% | 0.33 | Powder | frond |
| Cehami | *Centipeda Cunninghamii* | 0.66% | 0.33 | Powder | leaves |
| Amla | *Phyllanthus emblica* | 0.33% | 0.165 | Powder | fruit |
| AFA | *Aphanizomenon flos-aquae* | 0.66% | 0.33 | Powder | whole plant |
| Pomegranate | *Punica Granatum* | 0.66% | 0.33 | Powder | fruit |
| Sangre de drago | *Croton lechleri* | 0.66% | 0.33 | Powder | sap |
| Guar | *Cyamopsis tetragonolobus* | 0.33% | 0.165 | Powder | seed |
| Vanilla | *Vanilla planifolia* | 0.33% | 0.165 | Powder | bean |
| Colostrum | first milk | 0.33% | 0.165 | Powder | milk |
| Cytokines | *E. coli* | 0.10% | 0.05 | Aqueous | cultures |
| Maqui | *Aristotelia Chilensis* | 0.50% | 0.25 | Powder | berries |
| Synergy berries | 12 berries | 0.50% | 0.25 | Powder | berries |
| Green Tea Extract | *Camellia sinensis* | 0.50% | 0.25 | Powder | leaf |
| Vanilla 20 fold extract | *Vanilla planifolia* | 0.22% | 0.11 | Powder | bean |
| Cacao | *Theobroma Cacao* | 0.20% | 0.1 | Powder | bean |
| Olive extract (Hydroxytyrolosol) | *Olea europaea* | 0.25% | 0.125 | Powder | fruit |
| Vitamin E (Sunflower) | *Helianthus annuus* | 0.8% | 0.4 | oil | seed |
| Samambaia | *Polypodium leucotomos* | 0.5% | 0.25 | Powder | leaf |
| Bulgarian Rose | *Rosa Damascena* | 0.22% | 0.11 | oil | flower |
| Jasmine | *Jasminum Grandiflorum* | 0.24% | 0.12 | oil | flower |
| Sweet Orange | *Citrus Sinensis* | 0.40% | 0.2 | oil | peel |
| Ylang-ylang | *Cananga Odorata* | 0.12% | 0.06 | oil | flower |
| Tangerine Essential Oil | *Citrus Reticulata* | 0.01% | 0.005 | oil | peel |
| Bitter Orange extract | *Citrus aurantium* | 1.25% | 0.625 | Aqueous | seed |
| Honeysuckle | *Lonicera Japonica* | 1.25% | 0.625 | Aqueous | flower |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the sources of natural ingredients and constituent products, combinations of natural ingredients therein, the manufacturing techniques used to create cosmetic products, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of conditioning the skin of a subject in need thereof, comprising:
   topically administering to the skin of said subject a skin care composition comprising effective amounts of:
   *Aphanizomenon flos-aquae* or an extract thereof;
   *Aloe* or an extract thereof;
   fucoidan or an extract thereof;
   *Theobroma cacao* or an extract thereof;
   *Vanilla* or an extract thereof;
   *Centipeda cunninghamii* or an extract thereof;
   *Croton lechleri* or an extract thereof;
   *Aristotelia chilensis* or an extract thereof; and
   one or more components selected from the group consisting of: *Moringa oleifera* or an extract thereof, soy or an extract thereof, *Cyathea medularis* or an extract thereof, *Phyllanthus emblica* or an extract thereof, *Punica granatum* or an extract thereof, colostrum or an extract thereof, *Citrus aurantium* or an extract thereof, *Lonicera japonica* or an extract thereof, *Olea europaea* or an extract thereof, *Polypodium leucotomos* or an extract thereof, *Camellia sinensis* or an extract thereof, berries or an extract thereof, *Cocos nucifera* or an extract thereof, *Vitellaria nilotica* or an extract thereof, *Rosa rubiginosa* or an extract thereof, *Ceteryl olivate* or an extract thereof, *Glycine max* or an extract thereof, *Citrus sinensis* or an extract thereof, *Quillaja saponaria* or an extract thereof, *Helianthus annuus* or an extract thereof, N-acetylglucosamine 6-phosphate (NAG6P), *E. coli* or an extract thereof, *Rosa damascena* or an extract thereof, *Jasminum grandiflorum* or an extract thereof, *Cananga odorata* or an extract thereof, and/or *Citrus reticulata* or an extract thereof, wherein said berries consist of one or more of the following: Wild Bilberry, Wild Ligonberry, Black Currant, Aronia, Pomegranate, Wild Blueberry, Concorde Grape, Sour Cherry, Wild Elderberry, Wild Cranberry, Red Raspberry, and Black Raspberry,
   in an amount sufficient to condition the skin of the subject.

2. The method of conditioning of claim 1, wherein conditioning the skin of the subject comprises an increase in progenitor cell, stem cell, and/or dermal fibroblast proliferation.

3. The method of conditioning of claim 1, wherein conditioning the skin of the subject comprises an increase in progenitor cell, stem cell, and/or dermal fibroblast mobilization.

4. The method of conditioning of claim 1, wherein conditioning the skin of the subject comprises an increase in progenitor cell, stem cell, and/or dermal fibroblast migration.

5. The method of conditioning of claim 1, wherein conditioning the skin of the subject comprises an increase in antioxidant protection.

6. The method of conditioning of claim 1, wherein conditioning the skin of the subject comprises inhibition of free radical formation.

7. The method of claim 5, wherein the improved skin appearance comprises improved skin tone.

8. The method of claim 5, wherein the improved skin appearance comprises improved skin elasticity.

9. The method of claim 5, wherein the improved skin appearance comprises enhanced skin thickness.

10. The method of claim 5, wherein the improved skin appearance comprises improved skin hydration.

11. A method of improving skin appearance in a subject in need thereof, comprising:
    topically administering to the skin of said subject a skin care composition comprising effective amounts of:
    *Aphanizomenon flos-aquae* or an extract thereof;
    *Aloe* or an extract thereof;
    fucoidan or an extract thereof;
    *Theobroma cacao* or an extract thereof;
    *Vanilla* or an extract thereof;
    *Centipeda cunninghamii* or an extract thereof;
    *Croton lechleri* or an extract thereof;
    *Aristotelia chilensis* or an extract thereof; and
    one or more of the following components selected from the group consisting of: *Moringa oleifera* or an extract thereof, soy or an extract thereof, *Cyathea medularis* or an extract thereof, *Phyllanthus emblica* or an extract thereof, *Punica granatum* or an extract thereof, colostrum or an extract thereof, *Citrus aurantium* or an extract thereof, *Lonicera japonica* or an extract thereof, *Olea europaea* or an extract thereof, *Polypodium leucotomos* or an extract thereof, *Camellia sinensis* or an extract thereof, berries or an extract thereof, *Cocos nucifera* or an extract thereof, *Vitellaria nilotica* or an extract thereof, *Rosa rubiginosa* or an extract thereof, *Ceteryl olivate* or an extract thereof, *Glycine max* or an extract thereof, *Citrus sinensis* or an extract thereof, *Quillaja saponaria* or an extract thereof, *Helianthus annuus* or an extract thereof, N-acetylglucosamine 6-phosphate (NAG6P), *E. coli* or an extract thereof, *Rosa damascena* or an extract thereof, *Jasminum grandiflorum* or an extract thereof, *Cananga odorata* or an extract thereof, and/or *Citrus reticulata* or an extract thereof, wherein said berries consist of one or more of the following: Wild Bilberry, Wild Ligonberry, Black Currant, Aronia, Pomegranate, Wild Blueberry, Concorde Grape, Sour Cherry, Wild Elderberry, Wild Cranberry, Red Raspberry, and Black Raspberry, in an amount sufficient to improve skin appearance in a subject.

12. A method of reducing age-related features in the skin of a subject in need thereof, comprising:

topically administering to the skin of said subject a skin care composition comprising effective amounts of:
*Aphanizomenon flos-aquae* or an extract thereof;
*Aloe* or an extract thereof;
fucoidan or an extract thereof;
*Theobroma cacao* or an extract thereof;
*Vanilla* or an extract thereof;
*Centipeda cunninghamii* or an extract thereof;
*Croton lechleri* or an extract thereof;
*Aristotelia chilensis* or an extract thereof; and
one or more components selected from the group consisting of: *Moringa oleifera* or an extract thereof, soy or an extract thereof, *Cyathea medularis* or an extract thereof, *Phyllanthus emblica* or an extract thereof, *Punica granatum* or an extract thereof, colostrum or an extract thereof, *Citrus aurantium* or an extract thereof, *Lonicera japonica* or an extract thereof, *Olea europaea* or an extract thereof, *Polypodium leucotomos* or an extract thereof, *Camellia sinensis* or an extract thereof, berries or an extract thereof, *Cocos nucifera* or an extract thereof, *Vitellaria nilotica* or an extract thereof, *Rosa rubiginosa* or an extract thereof, *Ceteryl olivate* or an extract thereof, *Glycine max* or an extract thereof, *Citrus sinensis* or extra an extract is thereof, *Quillaja saponaria* or an extract thereof, *Helianthus annuus* or an extract thereof, N-acetylglucosamine 6-phosphate (NAG6P), *E. coli* or an extract thereof, *Rosa damascena* or an extract thereof, *Jasminum grandiflorum* or an extract thereof, *Cananga odorata* or extr an extract acts thereof, and/or *Citrus reticulata* or an extract thereof, wherein said berries consist of one or more of the following: Wild Bilberry, Wild Ligonberry, Black Currant, Aronia, Pomegranate, Wild Blueberry, Concorde Grape, Sour Cherry, Wild Elderberry, Wild Cranberry, Red Raspberry, and Black Raspberry, in an amount sufficient to reducing age-related features in the skin of a subject.

13. The method of claim 12, wherein the age-related features comprise wrinkles.

14. The method of claim 12, wherein the age-related features comprise fine lines.

15. The method of claim 12, wherein the age-related features comprise dark patches of skin or age spots.

* * * * *